United States Patent
Jamiolkowski et al.

(10) Patent No.: US 11,058,792 B2
(45) Date of Patent: Jul. 13, 2021

(54) READILY ABSORBABLE COPOLYMER COMPOSITIONS FOR HIGH STRENGTH SUTURES HAVING ENHANCED STRENGTH RETENTION POST-IMPLANTATION

(71) Applicant: Ethicon, Inc., Somerville, NJ (US)

(72) Inventors: Dennis D. Jamiolkowski, Long Valley, NJ (US); Christopher DeFelice, Springfield, NJ (US); Sasa Andjelic, Nanuet, NY (US); Brian M. Kelly, Ringoes, NJ (US); Marc Wisnudel, Millburn, NJ (US); Daniel Steiger, Basking Ridge, NJ (US); Gaoyuan Gavin Chen, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 16/021,322

(22) Filed: Jun. 28, 2018

(65) Prior Publication Data
US 2020/0000958 A1 Jan. 2, 2020

(51) Int. Cl.
| | |
|---|---|
| *A61L 17/12* | (2006.01) |
| *A61L 17/00* | (2006.01) |
| *A61L 17/14* | (2006.01) |
| *C08G 63/64* | (2006.01) |
| *A61B 17/06* | (2006.01) |
| *C08G 63/08* | (2006.01) |
| *A61B 17/00* | (2006.01) |

(52) U.S. Cl.
CPC ........ *A61L 17/12* (2013.01); *A61B 17/06166* (2013.01); *A61L 17/005* (2013.01); *A61L 17/145* (2013.01); *C08G 63/64* (2013.01); *A61B 2017/00004* (2013.01); *A61L 2300/404* (2013.01); *C08G 63/08* (2013.01)

(58) Field of Classification Search
None
See application file for complete search history.

(56) References Cited

U.S. PATENT DOCUMENTS

| | | | |
|---|---|---|---|
| 3,839,297 A | 10/1974 | Wasserman | |
| 4,243,775 A | 1/1981 | Rosensaft et al. | |
| 5,133,739 A | 7/1992 | Bezwada et al. | |
| 5,236,444 A | 8/1993 | Muth et al. | |
| 6,007,565 A * | 12/1999 | Roby | A61L 17/12 606/228 |
| 6,048,947 A | 4/2000 | Oberhoffner | |
| 6,136,018 A | 10/2000 | Roby et al. | |
| 6,183,499 B1 * | 2/2001 | Fischer | A61B 17/06166 606/228 |
| 6,476,180 B1 | 11/2002 | Kapur | |
| 6,712,838 B2 | 3/2004 | D'Aversa et al. | |
| 6,770,717 B2 | 8/2004 | Kim et al. | |
| 7,913,365 B2 | 3/2011 | Genova et al. | |
| 8,216,497 B2 | 7/2012 | Lindh, Sr. et al. | |
| 8,481,651 B2 | 7/2013 | Hissink et al. | |
| 2004/0006199 A1 | 1/2004 | Newman | |
| 2004/0185250 A1 | 9/2004 | John | |
| 2008/0058869 A1 * | 3/2008 | Stopek | A61B 17/06166 606/228 |
| 2009/0304767 A1 | 12/2009 | Sikes et al. | |
| 2015/0045469 A1 | 2/2015 | Nichols | |

OTHER PUBLICATIONS

International Search Report dated Apr. 24, 2020 for International Application No. PCT/IB19/55179.

* cited by examiner

*Primary Examiner* — Brian Gulledge
(74) *Attorney, Agent, or Firm* — David R. Crichton

(57) ABSTRACT

Novel surgical sutures and novel medical devices made from novel semi-crystalline, glycolide-rich A-B-A triblock copolymers of glycolide and lactide, wherein said B-segment is a fully amorphous random copolymer of glycolide and lactide, for long term medical applications are disclosed. The novel polymer compositions are useful for long term absorbable surgical sutures, meshes and other medical devices, especially for patients with compromised healing. The novel sutures have improved properties and improved breaking strength retention, while still substantially absorbing within about a 120-day period post-implantation.

29 Claims, 13 Drawing Sheets

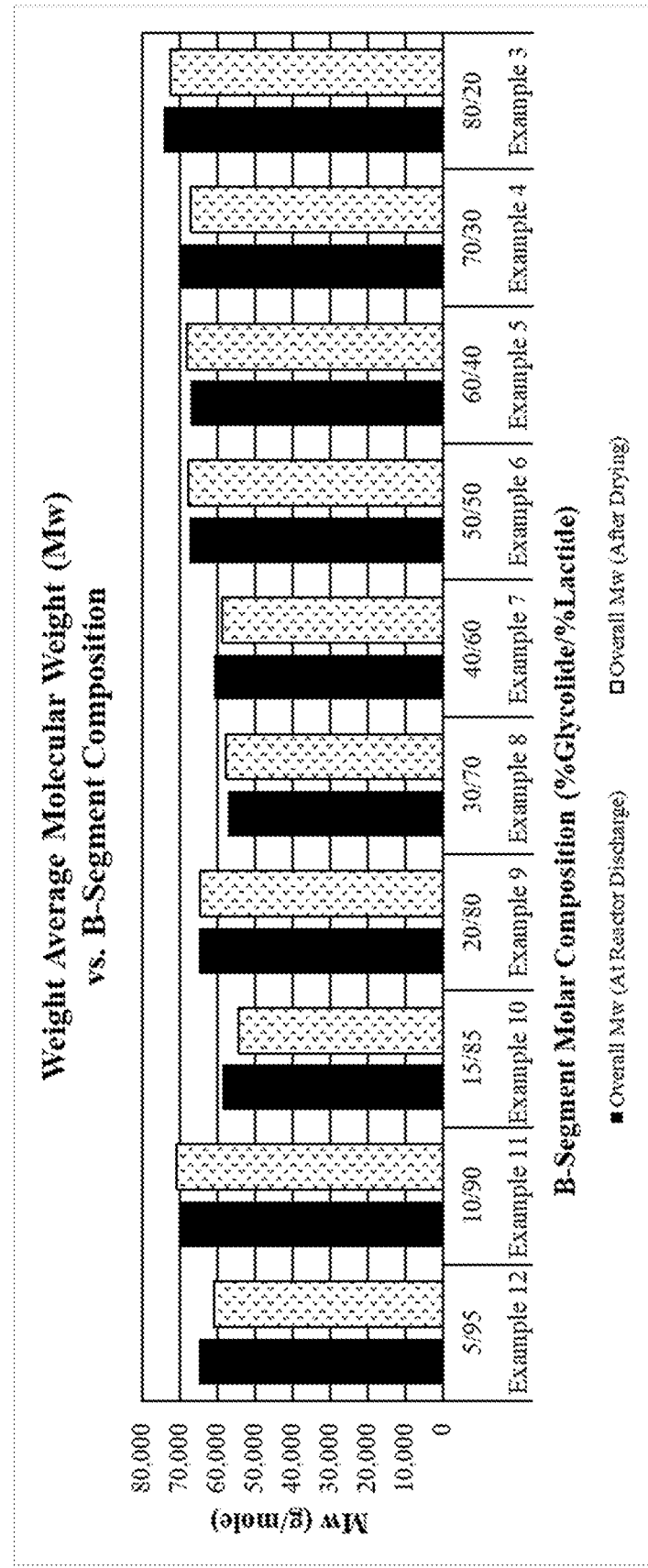
FIG. 1 – Weight Average Molecular Weight (Mw) of the A-B-A Polymers of Examples 3-12 vs. B-Segment Composition

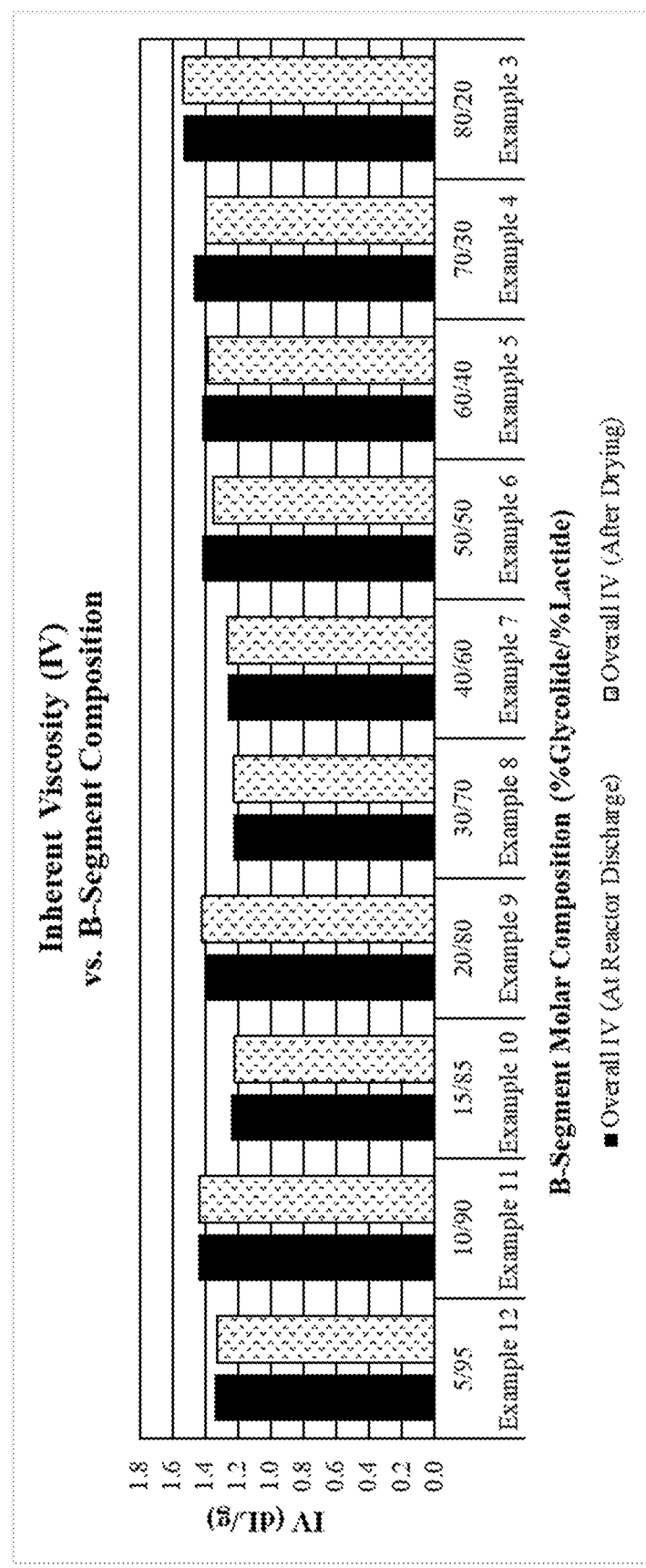
FIG. 2 – Inherent Viscosity (IV) of the A-B-A Polymers of Examples 3-12 vs. B-Segment Composition

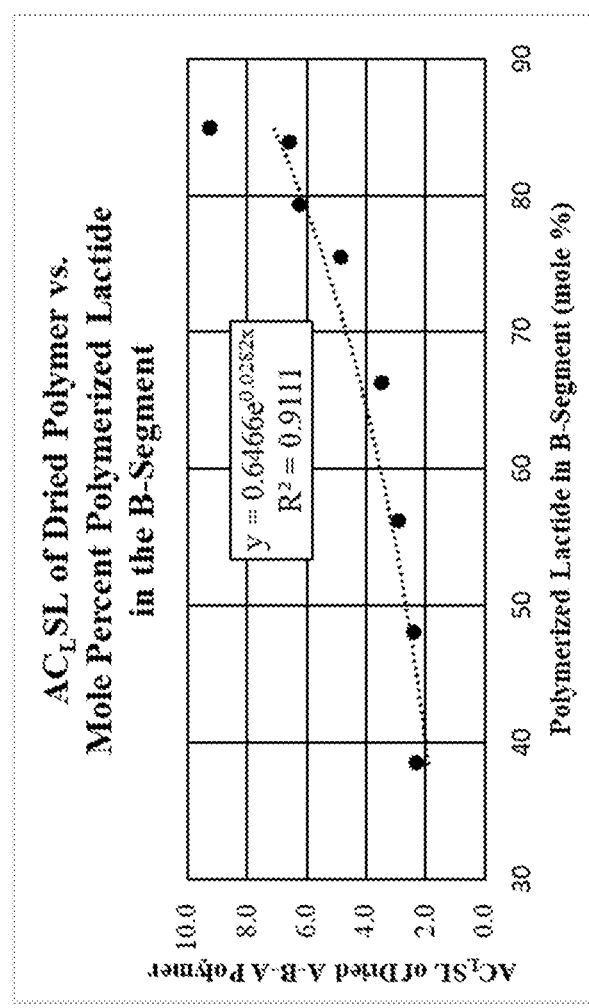
FIG. 3 – Average Chain Sequence Length of Lactoyl Units (AC$_L$SL) of the A-B-A Polymers of Examples 5-12 vs. Mole Percent Polymerized Lactide in the B-Segment

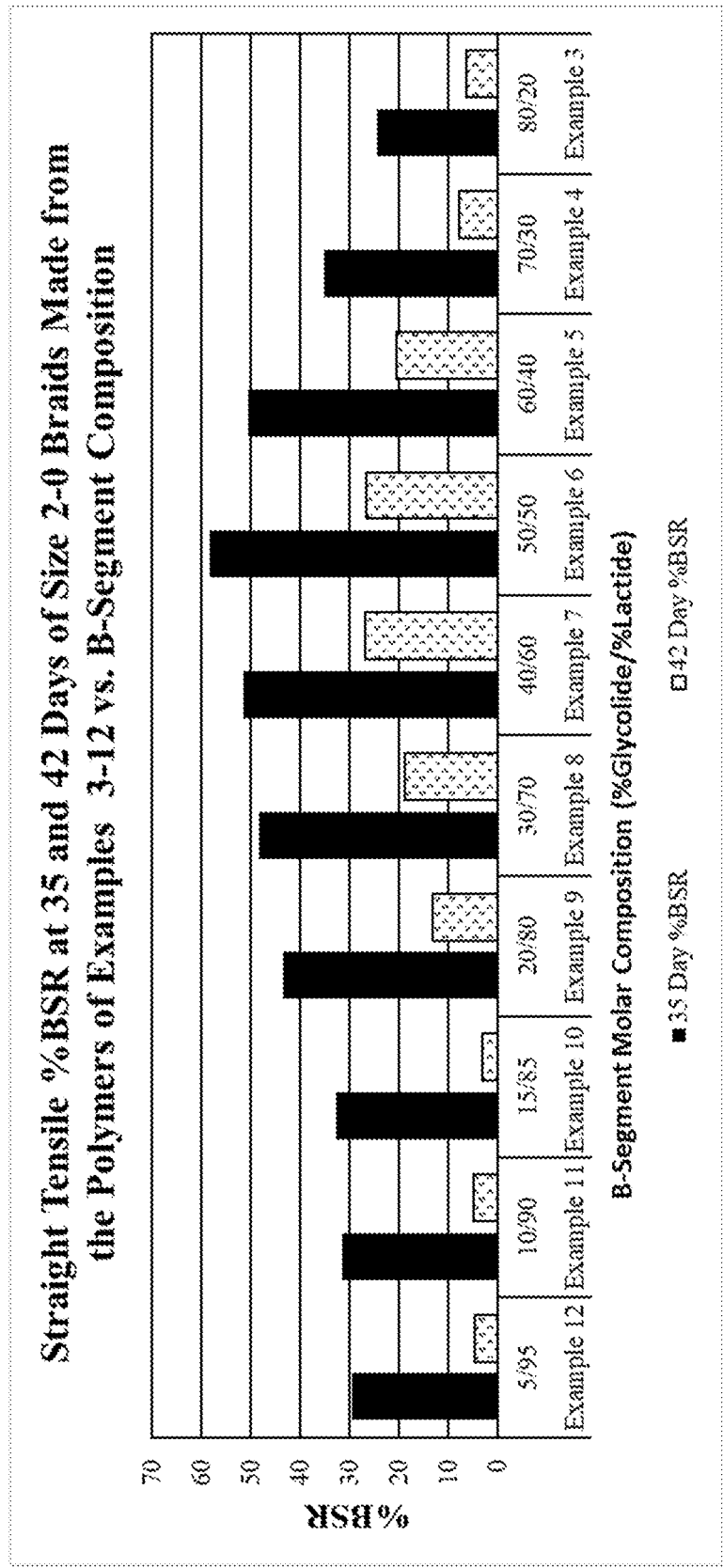
FIG. 4 – Straight Tensile Breaking Strength Retention (BSR) of Size 2-0 Braids Made from the A-B-A Polymers of Examples 3-12 vs. B-Segment Composition

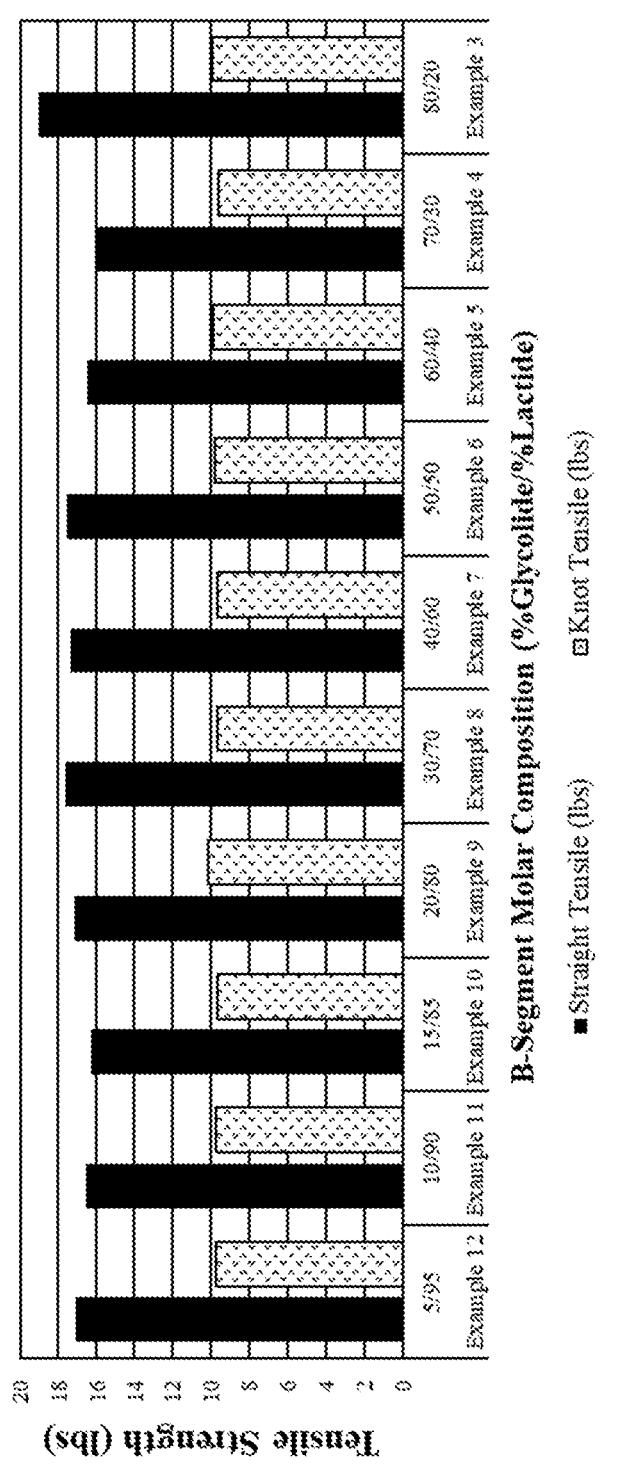
FIG. 5 – Tensile Strength of Size 2-0 Braids Made From the A-B-A Polymers of Examples 3-12 vs. "B" Segment Composition

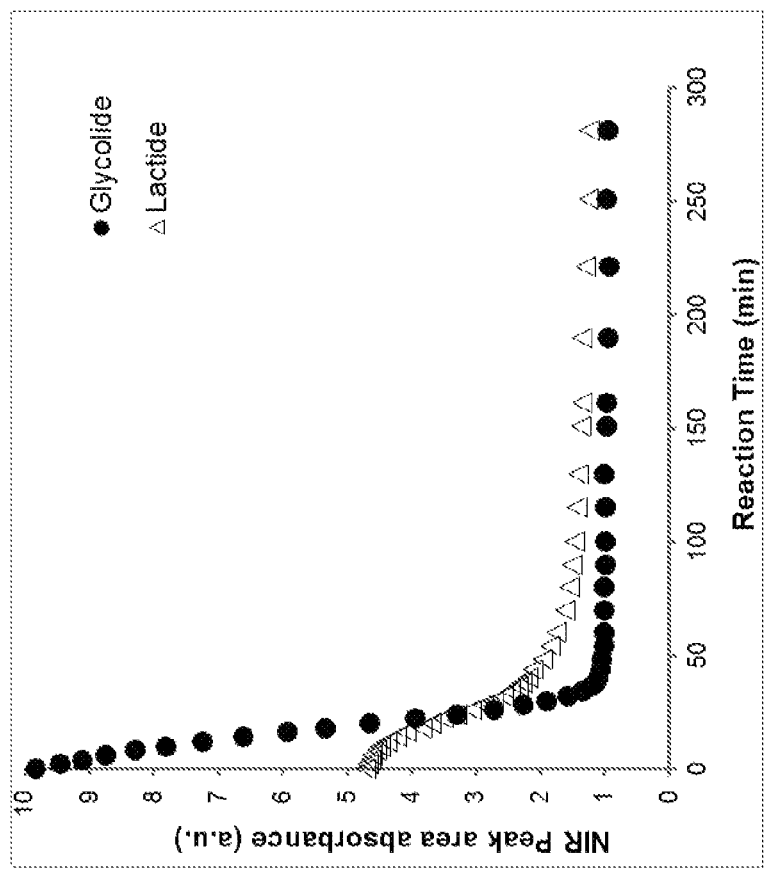
FIG. 6A - The First Stage Monomer Consumption by Real-Time FT-NIR Spectroscopy for Example 16 Showing the Area Under the Monomers' Peaks as a Function of Reaction Time

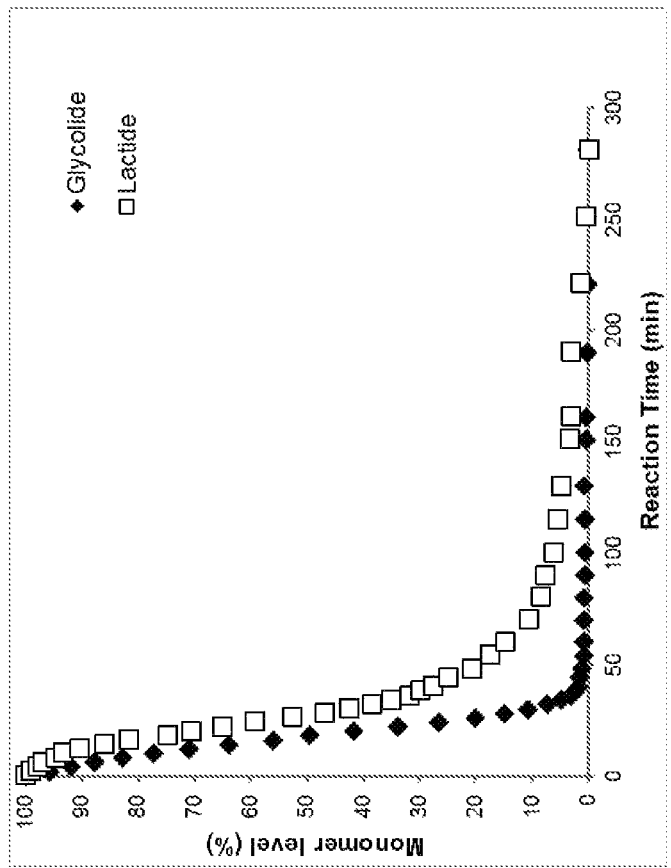
FIG. 6B - The First Stage Monomer Consumption by Real-Time FT-NIR Spectroscopy for Example 16 Showing Monomer Consumption in Percentages as a Function of Time

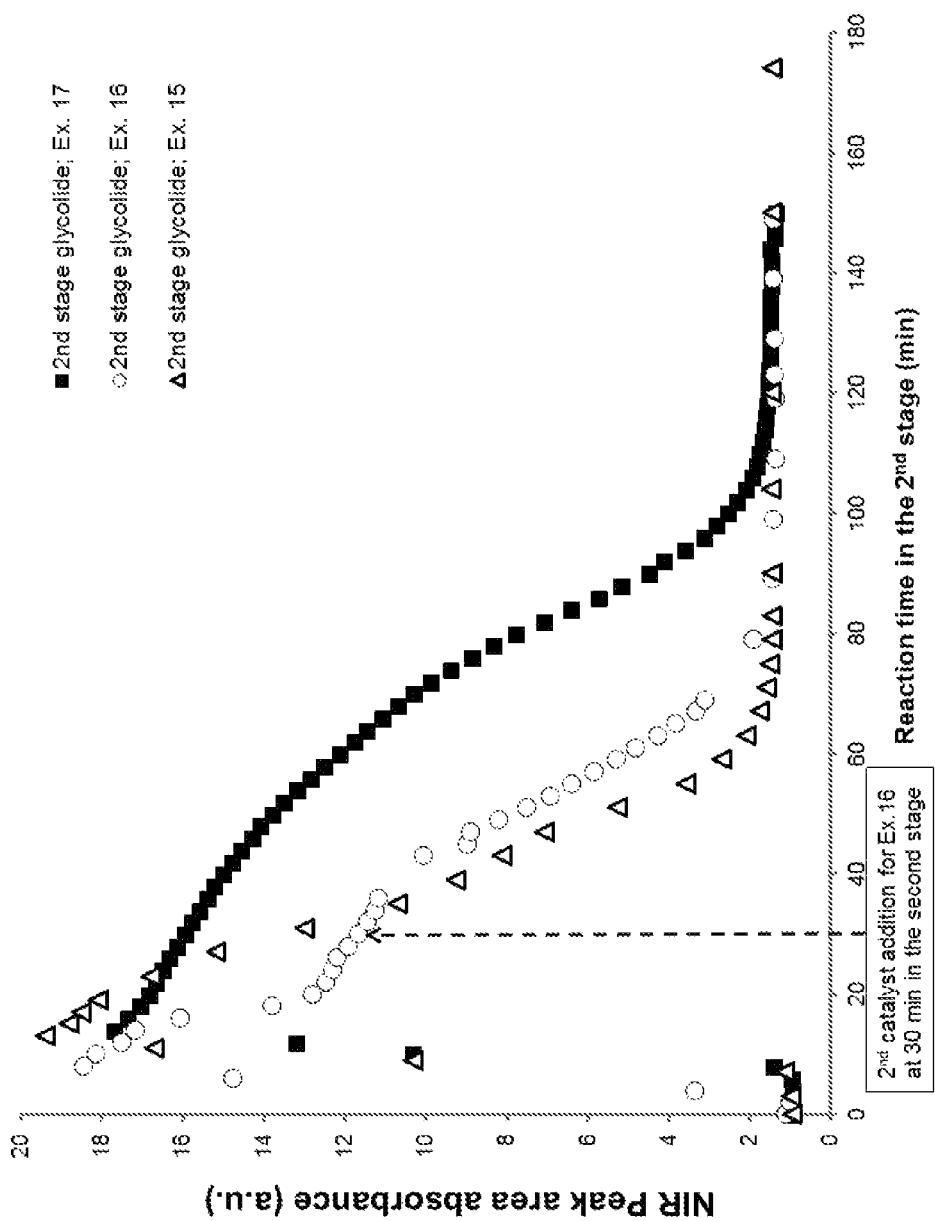
FIG. 7 – the Second Stage Glycolide Conversion for Examples 15-17

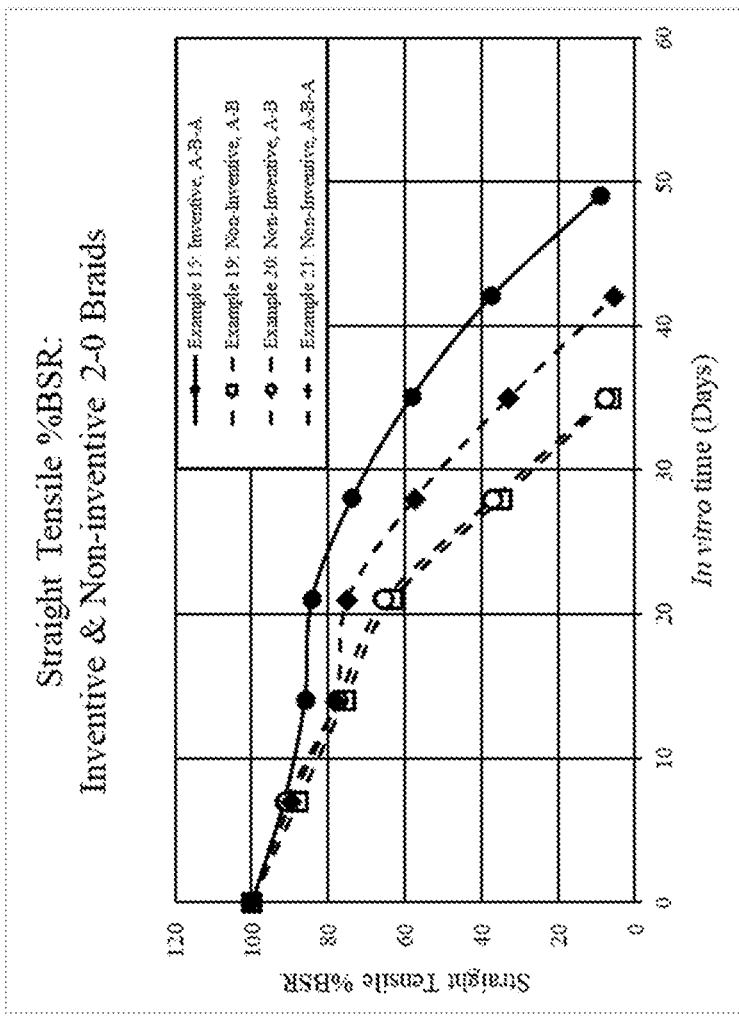
FIG. 8A - *In Vitro* Straight Tensile Percent BSR of a 2-0 Braid of the Current Invention (Made from the A-B-A Copolymer of Example 15), and 2-0 Braids Based on Prior Art Teachings (Made from the Copolymers of Examples 19-21)

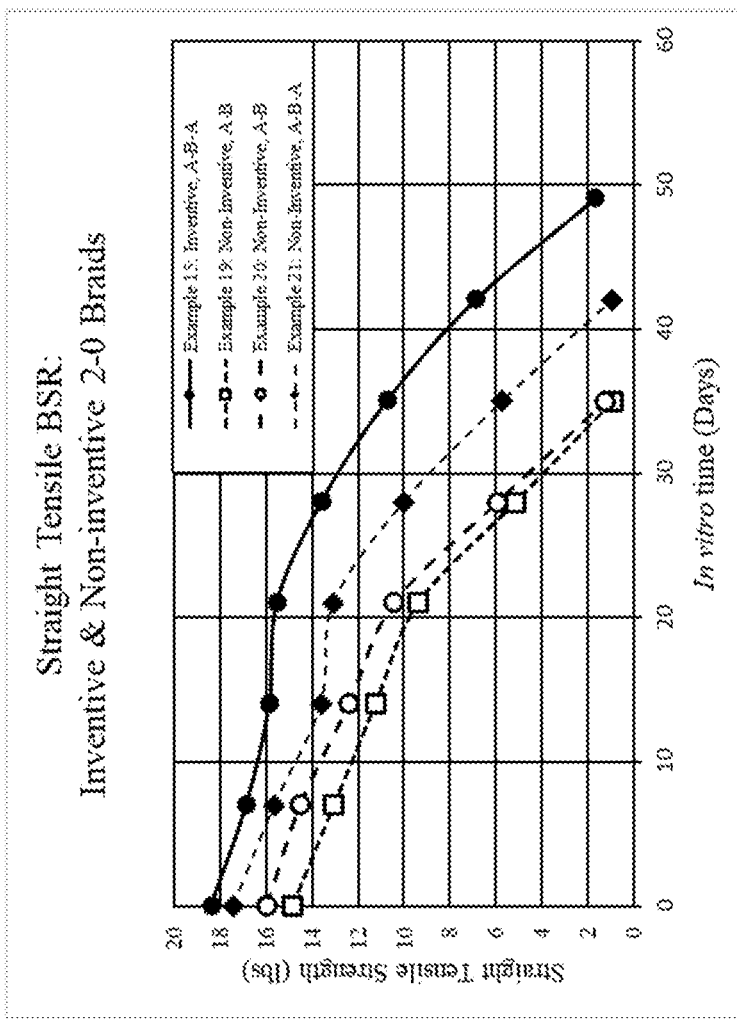
FIG. 8B - *In Vitro* Straight Tensile BSR, in Pounds, of a 2-0 Braid of the Current Invention (Made from the A-B-A Copolymer of Example 15), and 2-0 Braids Based on Prior Art Teachings (Made from the Copolymers of Examples 19-21)

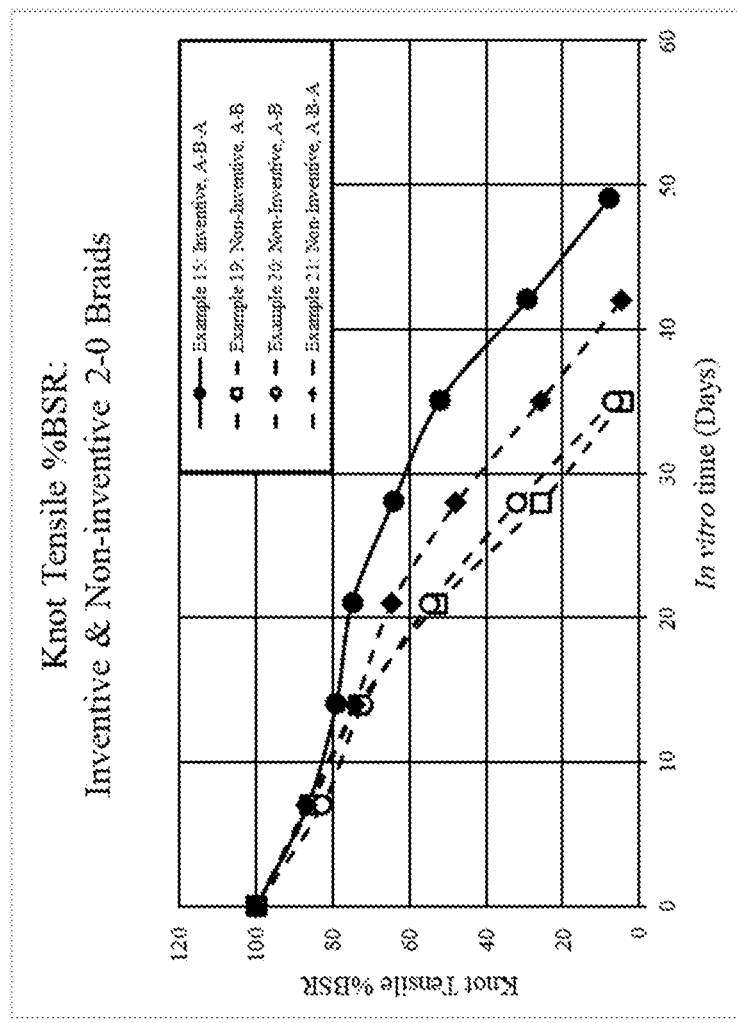
FIG. 9A - *In Vitro* Knot Tensile Percent BSR of a 2-0 Braid of the Current Invention (Made from the A-B-A Copolymer of Example 15), and 2-0 Braids Based on Prior Art Teachings (Made from the Copolymers of Examples 19-21)

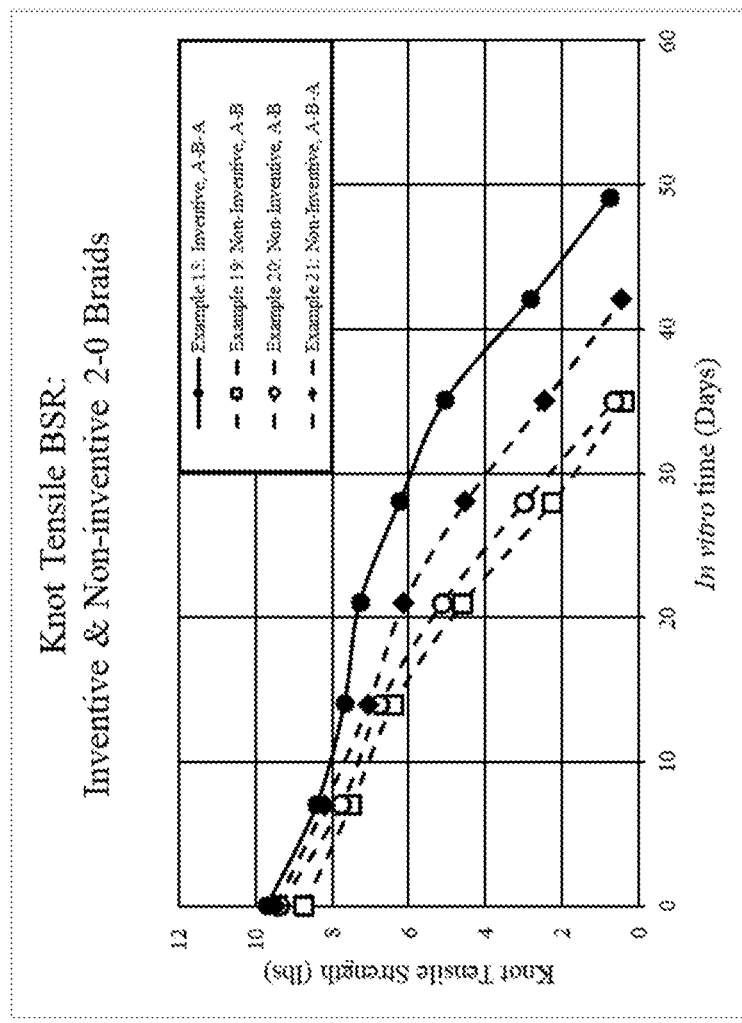
FIG. 9B - *In Vitro* Knot Tensile BSR, in Pounds, of a 2-0 Braid of the Current Invention (Made from the A-B-A Copolymer of Example 15), and 2-0 Braids Based on Prior Art Teachings (Made from the Copolymers of Examples 19-21)

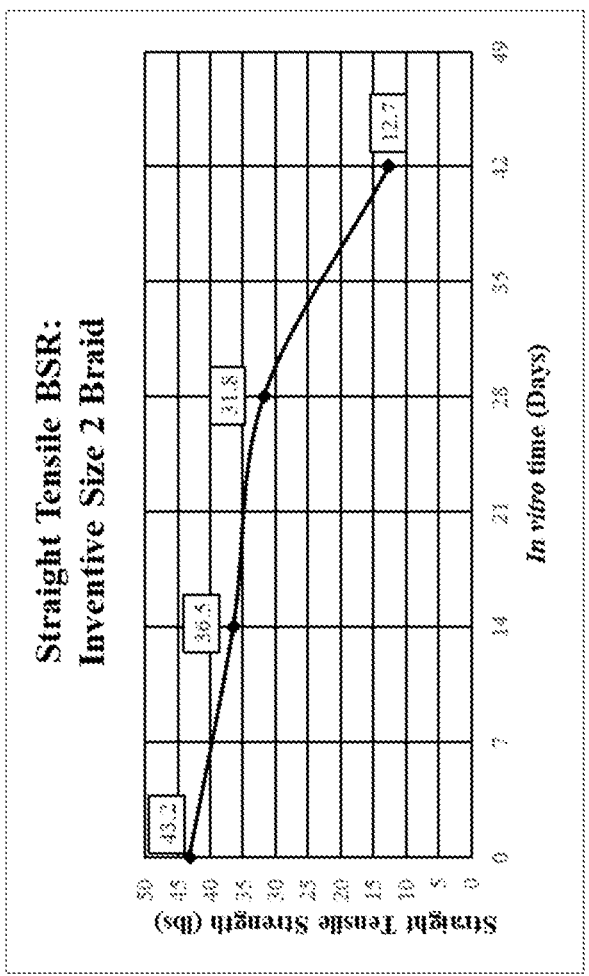
FIG. 10 - *In Vitro* Straight Tensile BSR, in Pounds, of a Size 2 Braid of the Current Invention (Made from the A-B-A Copolymer of Example 15)

READILY ABSORBABLE COPOLYMER COMPOSITIONS FOR HIGH STRENGTH SUTURES HAVING ENHANCED STRENGTH RETENTION POST-IMPLANTATION

FIELD OF THE INVENTION

This invention relates to novel absorbable sutures made from novel semi-crystalline, segmented A-B-A block copolymers of glycolide and lactide for longer term absorbable medical applications, and other implantable medical devices having enhanced strength retention post-implantation; the invention also relates to novel processes for making such sutures and copolymers.

BACKGROUND OF THE INVENTION

Synthetic absorbable polyesters are well known in the art. The open and patent literature particularly describe absorbable polymers and copolymers made from glycolide, L(−)-lactide, D(+)-lactide, meso-lactide, epsilon-caprolactone, p-dioxanone, trimethylene carbonate, and combinations thereof. The term absorbable is meant to be a generic term, which may also include bioabsorbable, resorbable, bioresorbable, degradable or biodegradable.

One very important application of absorbable polyesters is their use as surgical sutures. Absorbable sutures generally come in two basic forms, multifilament braids and monofilament fibers. Absorbable multifilament sutures have been made from glycolide homopolymer and lactide/glycolide copolymers. A very important aspect of any absorbable medical device is the length of time that its mechanical properties are retained in vivo. For example, in some surgical applications it is important for the medical device to retain strength for a considerable length of time to allow the body the time necessary to heal while performing its desired function. This is often referred to as Breaking Strength Retention (BSR). Sutures having longer BSR are particularly needed when addressing wound closure for patients having compromised healing. These include diabetic patients, geriatric patients, and possibly patients under chemotherapy. A need also exists in wound closure of bodily areas having poor or diminished blood supply.

Absorbable sutures with longer BSR are known and have been made from conventional polymers, and include, but are not limited to, multifilament (braided) sutures made from lactide-rich lactide/glycolide copolymers and monofilament sutures made from polydioxanone polymers. Although absorbable sutures with longer BSR are available, braided sutures made from lactide-rich lactide/glycolide copolymers exhibit significantly long total absorption time which can lead to undesirable outcomes. In addition, monofilament sutures with longer BSR exhibit relatively inferior handling and knot security properties due to their relatively higher stiffness and also typically exhibit significantly lower initial tensile strength compared to braided sutures. Those skilled in the art will appreciate that monofilament and multifilament absorbable sutures exist and that short term and long term absorbable sutures exist, and such sutures are available to the surgeon. However, there is a need for an absorbable polymer that can be made into an absorbable medical device such as a suture, wherein the suture would have a combination of high initial tensile strength, superb handling and first throw hold, good knot sliding and knot security, and long BSR performance for slow wound healing applications, and yet demonstrates complete absorption in a relatively short time, approximately 18 weeks or less. There is also a need for processes for converting such absorbable polymers into medical devices having these properties, including sutures.

Crystalline block copolymers of glycolide and lactide are disclosed in U.S. Pat. Nos. 6,007,565 and 6,136,018 (Roby et al.). The copolymers disclosed in these patents are described as preferably composed of two blocks (A-B type), with the first block containing from about 60 to 35 mole percent of glycolide randomly combined with from about 60 to 35 mole percent of lactide repeat units. The first block is described to preferably contain from about 40 to about 45 mole percent of lactic acid ester linkages. The second block is described as containing both glycolide and lactide repeating units, with a higher proportion of glycolide than the first block. The glycolide concentration in the entire copolymer ranges from about 75 to about 95 mole percent. Although the BSR properties of fibers made by these copolymers are somewhat longer than corresponding random glycolide and lactide copolymer compositions, they are vastly inferior to the BSR performance of the fibers made from the copolymers of the present invention, as will be shown later in the experimental section. Although a difunctional initiator was mentioned in the text as a possibility, Roby et al. failed to recognize the criticality in having an A-B-A block copolymer structure versus an A-B type, providing for a "B" segment center block (CB) composition that would allow for extra-long BSR properties. Furthermore, processing conditions (synthesis and extrusion) as described in both references are found to be inadequate in producing fibers that exhibit longer BSR properties.

Similarly, U.S. Pat. No. 4,243,775 teaches a method for the manufacture of surgical articles made from synthetic absorbable copolymers formed by copolymerizing glycolide as the predominant monomer with a cyclic ester other than glycolide employing sequential addition of the monomers in the polymerization. This reference teaches that, preferably, the cyclic ester monomer is lactide. One of the preferred embodiments includes triblock structures formed by sequentially and consecutively copolymerizing L(−)-lactide, glycolide, and again L(−)-lactide. The copolymer produced from this method has lactic acid units predominating on both ends of the glycolide CB polymer chain. In addition, it is believed that the presence of lactide moieties in the end blocks would reduce crystallization and therefore would very likely reduce the suture tensile strength. These structures, again, would not be suitable for long BSR suture applications.

Completely amorphous, biodegradable multi-block copolymers composed of a variety of lactone moieties including glycolide and lactide are described in U.S. Pat. No. 8,481,651B2. These copolymers have soft chain segments due to the absence of crystallinity and possess relatively low glass transition temperature. Thus, they cannot be used to produce strong sutures with long BSR properties and sufficient dimensional stability due to the lack of crystallinity and relatively low glass transition temperature.

U.S. Pat. No. 6,770,717 describes a biodegradable multi-block copolymer, whose repeat units, in addition to glycolide and glycolide/lactide combinations, contain poly(epsilon-caprolactone) (PCL) moieties. The presence of flexible and hydrophobic PCL units may improve elasticity and increase material hydrophobicity for tissue engineering applications, however, the significantly lower crystallinity would result in a suture device with lower tensile strength.

Absorbable multi-block compositions, wherein the first block is a poly(lactide-glycolide) and the second block is a member of the group consisting of lactide-glycolide copolymer having a higher percentage of lactide than the first block, are described in US 2009/304767. These high lactide block or graft compositions contain a first block having a lactide:glycolide ratio in the range of 25:75 to 60:40, and a second block having a lactide:glycolide ratio in the range of 70:30 to 99:1. These low crystallinity, low strength compositions may be suitable for coatings, scaffolds, and/or drug delivery carriers, but not for high strength long term suture applications.

U.S. Pat. No. 5,236,444 relates to absorbable block copolymers and surgical articles therefrom having a block that is predominately made from polymerized glycolide, and a block that has glycolide, lactide and trimethylene carbonate linkages. The presence of trimethylene carbonate in these A-B structures provides increased elasticity for monofilament suture use, but lowers tensile strength and increases the hydrolysis rate, which negatively affects BSR performance.

In summary, there is an unmet need in this art for novel absorbable sutures having a combination of good handling characteristics, high initial tensile strength, long BSR properties post-implantation, and a relatively short total absorption time of preferably 120 days or less. There is a further need in this art for novel absorbable polymer systems for manufacturing such sutures and other absorbable medical devices having these desirable characteristics.

SUMMARY OF THE INVENTION

Novel semi-crystalline, glycolide-rich block copolymers of glycolide and lactide of the structure A-B-A for longer term absorbable medical applications are disclosed. The absorbable copolymers have a structure A-B-A comprising end segments A and middle segment B. The end-segments A comprise polymerized glycolide and the middle segment B comprises polymerized glycolide and polymerized lactide. The middle segment B is fully amorphous and contains about 30 mole percent to about 80 mole percent of polymerized lactide, and about 20 mole percent to about 70 mole percent of polymerized glycolide. The total amount of polymerized glycolide in the absorbable copolymer is about 88 mole percent to about 92 mole percent of the absorbable copolymer and the total amount of polymerized lactide is about 8 mole percent to about 12 mole percent of the absorbable copolymer.

Another aspect of the present invention is an absorbable medical device made from an absorbable copolymer of the structure A-B-A comprising end segments A and middle segment B. The end-segments A comprise polymerized glycolide and the middle segment B comprises polymerized glycolide and polymerized lactide. The middle segment B is fully amorphous and contains about 30 mole percent to about 80 mole percent of polymerized lactide, and about 20 mole percent to about 70 mole percent of polymerized glycolide. The total amount of polymerized glycolide in the absorbable copolymer is about 88 mole percent to about 92 mole percent of said absorbable copolymer and the total amount of polymerized lactide is about 8 mole percent to about 12 mole percent of said absorbable copolymer.

Yet another aspect of the present invention is a method of extruding the novel copolymers of the present invention into multifilament yarns.

Still yet another aspect of the present invention is a method of manufacturing a medical device from said novel copolymers.

Surprisingly and unexpectedly, multifilaments made from the segmented, glycolide-rich, poly(glycolide-co-lactide) copolymers having an A-B-A type structure of the present invention, exhibit exceptionally long BSR properties, while also exhibiting a total absorption time, for example, of 18 weeks or less.

These and other aspects and advantages of the present invention will become more apparent from the following description and accompanying figures.

BRIEF DESCRIPTION OF THE DRAWINGS

FIG. 1 is graph showing Weight Average Molecular Weight (Mw) of the A-B-A Polymers of Examples 3-12 vs. B-Segment Composition.

FIG. 2 is a graph showing Inherent Viscosity (IV) of the A-B-A Polymers of Examples 3-12 vs. B-Segment Composition.

FIG. 3 is a graph of Average Chain Sequence Length of Lactoyl Units (ACLSL) of the A-B-A Polymers of Examples 5-12 vs. Mole Percent Polymerized Lactide in the B-Segment.

FIG. 4 is a graph of Straight Tensile Breaking Strength Retention (BSR) of Size 2-0 Braids Made from the A-B-A Polymers of Examples 3-12 vs. B-Segment Composition.

FIG. 5 is a graph of Tensile Strength of Size 2-0 Braids Made From the A-B-A Polymers of Examples 3-12 vs. "B" Segment Composition.

FIGS. 6A and 6B are graphs showing The First Stage Monomer Consumption by Real-Time FT-NIR Spectroscopy for Example 16: A) Area Under the Monomers' Peaks as a Function of Reaction Time; and, B) Monomer Consumption in Percentages as a Function of Time.

FIG. 7 is a graph showing the Second Stage Glycolide Conversion for Examples 15-17.

FIG. 8A is a graph showing In Vitro Straight Tensile Percent BSR of a 2-0 Braid of the Current Invention (Made from the A-B-A Copolymer of Example 15), and 2-0 Braids Based on Prior Art Teachings (Made from the Copolymers of Examples 19-21).

FIG. 8B is a graph showing In Vitro Straight Tensile BSR, in Pounds, of a 2-0 Braid of the Current Invention (Made from the A-B-A Copolymer of Example 15), and 2-0 Braids Based on Prior Art Teachings (Made from the Copolymers of Examples 19-21).

FIG. 9A is a graph showing In Vitro Knot Tensile Percent BSR of a 2-0 Braid of the Current Invention (Made from the A-B-A Copolymer of Example 15), and 2-0 Braids Based on Prior Art Teachings (Made from the Copolymers of Examples 19-21).

FIG. 9B is a graph showing In Vitro Knot Tensile BSR, in Pounds, of a 2-0 Braid of the Current Invention (Made from the A-B-A Copolymer of Example 15), and 2-0 Braids Based on Prior Art Teachings (Made from the Copolymers of Examples 19-21).

FIG. 10 is a graph showing In Vitro Straight Tensile BSR, in Pounds, of a Size 2 Braid of the Current Invention (Made from the A-B-A Copolymer of Example 15).

DETAILED DESCRIPTION OF INVENTION

The present invention is directed toward novel copolymers of glycolide and lactide and novel medical devices, particularly sutures, made from such copolymers having surprising and unexpected properties. More specifically, this class of copolymers rich in glycolide is made to have a blocky sequence distribution that is non-random and of an A-B-A type. In glycolide and lactide copolymers in which most of the material is based on glycolide, the glycolide containing end segments ("A") need to be as pure as possible to allow fast crystallization, as well as high crystallinity level. On the other hand, an amorphous center block (B-segment) needs to be rich in lactide to increase the hydrophobicity of the amorphous region, which slows the rate hydrolysis, and ultimately results in longer BSR.

Dimensional stability in a fiber used to manufacture a surgical suture is critically important to prevent shrinkage, both in the sterile package before use, as well as after surgical implantation in the patient's body (i.e., in vivo). Although the overall level of crystallinity and glass transition temperature (Tg) of the material plays a role in dimensional stability, it is important to realize that the rate of crystallization is also critical to processing. If a slow-to-crystallize material is processed, it is very difficult to achieve a desired level of crystallinity and desired molecular orientation during processing, which therefore, could reduce the tensile strength of a fiber. To increase the rate of crystallization of a copolymer of given overall chemical composition, a block structure, particularly of A-B-A type would be preferable over a random sequence distribution. In addition, it will be shown herein below that minimizing transesterification reactions to maintain the A-B-A chain structure during processing is critical to achieving longer BSR properties of the manufactured device.

We have unexpectedly discovered that the following polymer chain sequence, polymer formulation, and polymerization attributes contribute greatly and significantly to long BSR performance in glycolide-rich glycolide/lactide copolymers: a) A-B-A block copolymer architecture instead of A-B type, with an amorphous B-segment containing about 30 mole percent to 80 mole percent of polymerized lactide and 20 mole percent to 70 mole percent of polymerized glycolide; b) less than 2 mole percent unreacted lactide monomer at the completion of the prepolymer (B-segment) polymerization; c) a catalyst ratio (moles of monomers:moles of catalyst) in the range between 50,000:1 to 300,000:1; d) diol as an initiator with an initiator ratio (moles of monomers:moles of initiator) between 500:1 to 1,500:1; e) fast agitation in the mixing period of the second polymerization stage; and, f) controlled exotherm and relatively low reactor batch temperature during the second polymerization stage.

The novel A-B-A segmented copolymers of the present invention can be prepared by a two-stage polymerization reaction in which a lactide/glycolide prepolymer is polymerized in the first stage to make the B-segment, and a second stage that consists of polymerizing additional glycolide off of both ends of the B-segment prepolymer to make the A-segments of the final A-B-A polymer. More specifically, the first stage involves polymerizing all of the lactide monomers and a small amount of glycolide monomers at temperatures between about 170° C. and about 240° C. in a suitable, conventional reactor vessel. Temperatures between about 180° C. and about 195° C. are particularly advantageous. In the practice of the present invention, an initiator that is a diol, such as diethylene glycol, must be used for the present formulations to work well. The concentration of a diol as an initiator determines the molecular weight of the final copolymer. Typically, the initiator ratio (moles of monomer:moles of initiator) is set between about 500:1 to about 1,500:1. More typically, the initiator ratio range is about 600:1 to about 1,200:1. Preferably, the initiator ratio range will be set between 750:1 to 900:1. Suitable catalysts include conventional catalysts, such as stannous octoate. The catalyst ratios (moles monomer:moles catalyst) that may be used typically range from about 50,000:1 to about 300,000:1, more typically from about 75,000:1 to about 275,000:1, with a preferred range from about 100,000:1 to about 250,000:1, and the most preferred range from about 150,000:1 to about 200,000:1. The reaction time in the first stage can vary depending on the reactor temperature, but it is typically between 120 and 180 minutes. The reaction time will be sufficient to effectively polymerize both glycolide and lactide monomers, such that the unreacted lactide at the end of the first stage is less than about 2 mole percent.

After the completion of this first stage of the polymerization, the second (major) portion of glycolide can be added directly into the reactor in its powder form. Preferably, the second stage glycolide is added in the molten form from a suitable, conventional melt tank preheated at 120° C. During the second stage addition, the temperature in the main reactor can be maintained at the temperature of the first polymerization stage, preferably between 175° C. and 195° C., until the mixing of the added glycolide with a prepolymer is completed. Alternately, once the major portion of glycolide monomer is added, the temperature can be brought to a range of about 200° C. to about 210° C., maintained at this temperature for a sufficiently effective period of time (e.g., about 30 to 90 minutes), until the complete mixing stage is achieved. During the second stage polymerization, it was found that the mixing speed had an impact on final polymer properties. After the second stage glycolide monomer is added to the reactor, a sufficiently effective high mixing speed is needed to ensure that the glycolide monomer is incorporated into the prepolymer melt. It was shown that a mixing (agitation) speed of between 15 RPM (rotation per minute) to about 30 RPM for 30 to 90 minutes is sufficiently effective for the type of reactor that was used in this study for complete mixing of the added glycolide monomer and prepolymer melts.

The second stage total reaction time will be sufficiently effective to polymerize the glycolide monomer added in the second stage off both ends of the prepolymer chains thus creating an A-B-A chain sequence, and can vary from about 100 minutes to about 200 minutes from the time of glycolide addition. The batch temperature in the second stage will be sufficiently effective to polymerize second stage glycolide, and may be kept at about 200° C. to about 230° C. Preferably, the batch temperature in the second polymerization stage should be maintained between 205° C. and 215° C. The optimal second stage reaction time may be approximately 150 minutes to 240 minutes from the glycolide addition. The agitation speed after the mixing period is over can be reduced to a sufficiently effective speed, for example, about 5 RPM to about 10 RPM, until the end of reaction. Lower agitation speeds at the later stages of the reaction were found to help in reducing the degradation and/or transesterification reactions.

Polymerized resin from the reactor can be discharged into multiple conventional containers and stored in a nitrogen flow equipped conventional oven, or placed in a conventional freezer until further processing. The copolymer resin discharged in this fashion requires additional grinding and sieving operations before drying. Preferably, the polymerized resin can be discharged through a conventional pelletization step, such as underwater pelletization, and then the resulting produced pellets can be stored in the freezer, or in the oven under nitrogen atmosphere prior further use.

Polymer drying and devolatilization is usually the final step in the polymer synthesis. This step is needed to remove water (from underwater pelletization) and unreacted monomers from the polymer. If the unreacted monomers are not removed, undesirable consequences could result in both downstream processing and in the final medical device, such as increased tissue reaction and accelerated in vivo degradation leading to poor BSR performance. A twin shell, oil-heated Patterson-Kelly tumble dryer, or equivalent, can be conveniently used for devolatilization of monomers and moisture. Alternatively, a Fluidized Bed Dryer (FBD) can be used for the same purpose. It is believed that there is no discernible difference between the two processes other than somewhat improved cycle time using the FBD.

A typical tumble dryer process includes a vacuum drying cycle with the following heating steps, operated at vacuum levels<250 mTorr: a) 18 hours ambient; b) 24 hours heated @ 140° C.; and, c) four hours of cooling down. This drying cycle is proven to be effective in removing unreacted monomer, and the drying efficiency is comparable to the fluidized bed dryers. Alternatively, a lower temperature drying cycle can be used as well: a) 10 hours ambient; b) 40-48 hours heated @ 120° C.; and, c) four hours of cooling down. The dryer process conditions will be sufficient to effectively remove unreacted monomers.

It will be evident to one skilled in the art that various alternate polymerization approaches are possible that will produce the copolymers of the present invention. For example, the polymerization of the amorphous glycolide/lactide prepolymer (B-segment) can be made separately in a larger amount, stored, and used at a later time to complete the overall polymerization, in which the prepolymer is re-heated and the glycolide monomer required for the A-segments is added to perform the second stage of the reaction. Again, one skilled in the art can provide a variety of alternate and effective polymerization schemes.

Poly(glycolide-co-lactide) copolymers comprising a polymerized glycolide having a total molar level between about 88 percent to about 92 percent and a polymerized lactide molar level between about 8 percent to about 12 percent are particularly useful in the practice of the present invention. This class of copolymers, the poly(glycolide-co-lactide) family rich in glycolide, will preferably contain about 10 mole percent of polymerized lactide.

The copolymers of the present invention are semicrystalline in nature, having a crystallinity level ranging typically from about 30 to about 55 percent, more typically about 35 to about 45 percent, and preferably about 38 to about 42 percent. The copolymers will have a molecular weight sufficiently high to allow the medical devices made therefrom to effectively have the mechanical properties needed to perform their intended function. Typically, for example, the molecular weight of the copolymers of the subject invention will be such so as to exhibit inherent viscosities (IV) as measured in hexafluoroisopropanol (HFIP, or hexafluoro-2-propanol) at 25° C. and at a concentration of 0.1 g/dL typically between about 1.2 dL/g to about 2.5 dL/g. More typically, the IV range can be between about 1.25 dL/g to about 1.8 dL/g, and most preferably between about 1.3 dL/g to about 1.6 dL/g.

The copolymers of the subject invention can be melt extruded by a variety of processing means. Multifilament fiber formation can be accomplished by different means. Monofilament fiber formation is also possible by melt extrusion followed by extrudate drawing with or without annealing. Methods of manufacturing monofilament and multifilament braided sutures are disclosed in U.S. Pat. No. 5,133,739, entitled "Segmented Copolymers of epsilon-Caprolactone and Glycolide" and U.S. Pat. No. 6,712,838 entitled "Braided Suture with Improved Knot Strength and Process to Produce Same", which are incorporated by reference in their entirety herein.

The novel surgical sutures made from the novel copolymers of the present invention preferably are multifilaments or braids having a BSR at 42-days post-implantation greater than 10%, more preferably greater than 20%, and most preferably greater than 30%. We have clearly shown (see Example 23, FIGS. 8B and 9B) that segmented, block copolymers of 90/10 poly(glycolide-co-lactide) described in the prior art (U.S. Pat. Nos. 6,007,565 and 6,136,018) have BSR values at 42-days post-implantation of only about 5% or lower and are vastly inferior to the novel copolymers and fibers of the present invention.

In one embodiment, the medical devices made of the copolymers of the present invention may contain conventional active ingredients (and equivalents thereof), such as antimicrobials, antibiotics, therapeutic agents, hemostatic agents, radio-opaque materials, tissue growth factors, and combinations thereof. Particularly useful antimicrobials include Triclosan, PHMB, Octenidine, silver and silver derivatives or any other bio-active agent and the like.

In addition to sutures, the copolymers of the present invention may be used to manufacture conventional medical devices using conventional processes. For example, injection molding can be used after allowing the copolymer to crystallize in the mold; alternately, biocompatible nucleating agents might be added to the copolymer to reduce cycle time. The medical devices may include, the following conventional devices: tissue repair fabrics, meshes, suture anchors, stents, orthopedic implants, staples, tacks, fasteners, suture clips, etc.

Sutures made from the copolymers of the present invention may be used in a conventional manner in conventional surgical procedures and equivalents thereof, e.g., to approximate tissue or affix tissue to medical devices. Typically, after a patient is prepared for surgery in a conventional manner, including swabbing the outer skin with antimicrobial solutions and anesthetizing the patient, the surgeon will make the required incisions, and, after performing the required procedure proceed to close the incision by approximating tissue using the novel sutures having longer BSR of the present invention made from the novel copolymers of the present invention. In addition to tissue approximation, the sutures may be used to affix implanted medical devices to tissue in a conventional manner. The longer-BSR absorbable sutures of the present invention implanted in the patient retain their strength in vivo for an extended period of time to allow for effective healing and recovery.

As discussed herein, suitable synthetic absorbable polymers of the present invention include glycolide/lactide segmented A-B-A type copolymers rich in glycolide, wherein the B-segment is a copolymer of glycolide and lactide. This B-segment will typically contain between about 30 mole percent and about 80 mole percent of polymerized lactide to make the B-segment fully amorphous, more typically about 40 to about 70 mole percent, and preferably about 50 to about 60 mole percent. Within this class, the copolymers rich in polymerized glycolide will typically have between about 80 to about 95 mole percent of total polymerized glycolide in the final copolymer, more typically about 84 to about 93 mole percent, and preferably about 88 to about 92 mole percent.

The medical devices made from the copolymers of the present invention may contain, if desired, medically useful substances. The medically useful substances may be incorporated into or onto the medical devices in a variety of conventional manners including compounding, coating, spraying, dipping, sputtering and the like. If desired, the medical devices of the present invention may contain other conventional medically useful components and agents. The other components, additives or agents will be present to provide additional desired characteristics to the multifilament or monofilament sutures and other medical devices of the present invention including but not limited to antimicrobial properties, controlled drug elution, therapeutic aspects, radio-opacification, and enhanced osseointegration, etc.

Such other components, additives and agents will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent.

Examples of antimicrobial agents useful with the sutures of the present invention include the polychlorophenoxy phenols such as 5-chloro-2-(2,4-dichlorophenoxy)phenol (also known as Triclosan). Examples of radio-opacification agents include barium sulfate while examples of osseointegration agents include tricalcium phosphate.

The variety of therapeutic agents that can be used with the medical devices and polymers systems of the present invention is vast. In general, therapeutic agents which may be administered via the medical device and polymer systems pharmaceutical combinations of the present invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro, in vivo clinical methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics that may be incorporated into the medical devices of the present invention include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Surgical sutures made from the copolymers of the present invention may also include other conventional additives including colorants such as pigments and dyes, as well as radio-opaque agents, growth factors and the like. The dyes should be generally acceptable for clinical use with absorbable polymers; this includes, without limitation, D&C Violet No. 2 and D&C Blue No. 6 and similar combinations thereof. Additional dyes that are useful include conventional dyes useful with absorbable polymers including D&C Green No. 6, and D&C Blue No. 6.

In addition, monofilament or multifilament sutures made from the copolymers of the present invention may be delivered to the surgeon in a variety of lengths and diameters. Preferably, conventional surgical needles are mounted to one end or both ends of the sutures (i.e., single-armed or double-armed), although the sutures may be unarmed with no surgical needles mounted.

Modern surgical sutures generally range from USP Size 5 (for example, heavy braided suture for orthopedics) to USP Size 11-0 (for example, fine monofilament suture for ophthalmics). The actual suture diameter for a given USP size differs depending on the suture material class. The diameters of sutures in the synthetic absorbable suture class are listed in the United States Pharmacopeia (USP) as well as in the European Pharmacopoeia. The USP standard is more commonly used. The novel sutures of the present invention can be made in a variety of sizes, including conventional suture sizes. The suture sizes of the braid sutures of the present invention, in general, can range from USP size 12-0 to 5. Multifilament braided sutures are constructed of filaments of the present invention and will have a sufficiently effective denier per filament (dpf) to provide the desired properties, typically a dpf of about 0.5 to about 5.

The novel sutures of the present invention may be packaged in conventional suture packaging including polymer trays with tracks, paper folders, etc., with a polymer and/or foil overwrap that is hermetically sealed and impervious to moisture and microbes. The sutures will be sterilized preferably in their packages using conventional medical device sterilizations processes, such as ethylene oxide, radiation, autoclaving, etc. Those skilled in the art will understand that the optimal sterilization process chosen should not adversely affect the characteristics of the absorbable polymeric sutures.

The novel absorbable sutures of the present invention that are made from the novel absorbable copolymers are preferably useful as multifilament surgical sutures. However, the filaments may be used in other conventional medical devices including, but not limited to, fibrous devices such as monofilament-based sutures and surgical fabrics including barbed sutures, meshes, woven fabrics, nonwoven fabrics, knitted fabrics, fibrous bundles, cords, tissue engineering substrates, and the like. The surgical meshes may be made using conventional methods including knitting, weaving, air-laying, etc. Filaments of the present invention, when used for constructing other medical devices such as meshes, will typically have diameters in the range of about 1 to about 100 µm.

Medical devices made from the novel segmented copolymers of the present invention may be used in conventional surgical procedures using conventional surgical techniques. For example, surgical sutures made from the novel copolymers of the present invention that are mounted to conventional surgical needles may be used to suture wounds, repair blood vessels and organs, close incisions, attach medical devices to tissue, etc. In the case of repairing wounds or closing incisions by approximating tissue edges about a wound or incision, the needle and suture are passed through tissue about the wound or incision one or more times, and the sides of the wound are brought together by tensioning the suture and securing it in place in a conventional manner such as with knots.

If desired, the copolymers of the present invention when made into monofilament sutures may be processed to have barbs. Such barbs can be emplaced or incorporated in a conventional manner including cutting, molding, pre-forming, forming, attaching, etc. An example of a barb-forming process is disclosed in the U.S. Pat. No. 8,216,497 "Tissue Holding Devices and Methods for Making the Same" which is incorporated herein by reference. An alternate process of making barbed sutures is a cutting process. An example of a barb-cutting process is disclosed in the U.S. Pat. No. 7,913,365 "Method of Forming Barbs on a Suture and Apparatus for Performing Same".

Different characterization methods, described below, were used to measure key properties of the polymer resins, fibers, and braids produced to support this application.

Calorimetric data were generated on a TA Instruments' Differential Scanning Calorimeter, DSC Model 2910 MDSC, using dry N2 as a purge gas. Typically, about 5-10 mg of a polymer resin or a fiber was placed in an aluminum pan, secured by a lid (cover), and positioned in the autosampler holder area of the instrument. Two types of non-isothermal conditions are employed: a) First heat scan: a copolymer or a fiber was quenched to −40° C., followed by the constant heating rate at 10° C./min up to 260° C.; and, b) Second heat scan: after melting of a sample at 260° C. for three minutes, a copolymer or a fiber was quenched below its glass transition temperature (−40° C.), followed by the controlled heating step with the constant rate of 10° C./min. The first heat scan data are indicative of "as is" properties of a sample and, as such, largely dependent on its thermal history. The second heat data, on the other hand, are independent of thermal history of the sample and are a function of the inherent properties of the sample (chemistry, molecular weight, monomer level, etc.). From the first heat scan data, in addition to the glass transition temperature and melting point, the heat of fusion, $\Delta Hm$, as an area under the melting peak and expressed typically in J/g, can be obtained. Heat of fusion is directly proportional to the level of crystallinity in a sample. The TA Universal Analysis 2000 (version 4.7A) software package provided by TA Instruments—Waters LLC was used to determine all calorimetric parameters. The mid-point of the step transition was used to obtain the glass transition data.

Morphological data were obtained by conventional Wide Angle X-Ray Diffraction (WAXD) analysis. The WAXD measurements of a dried resin or a fiber were carried out on a Siemens Hi-Star™ unit using CuKα radiation at a wavelength of 1.542 Å. The instrument was operated at 40 kV and 40 mA with a collimator size of Ø0.5 mm. The convolution of the X-ray images and the calculation of crystallinity content were conducted using the DIFFRAC PLUS™ software developed by Siemens.

Inherent viscosity, IV measurements were conducted in hexafluoroisopropanol, HFIP at 25° C. and at a concentration of 0.10 g/dL. The molecular weight measurements were performed using Gel Permission Chromatography equipped with Wyatt's Optilab rEx refractometer and Wyatt's HELEOS II multi-angle laser light scattering detector. During the measurements, PL HFIP gel columns were maintained at 40° C., with a mobile phase consisting of HFIP with 0.01M LiBr (0.2% $H_2O$) operating at the flow rate of 0.7 ml/min.

Gel Permeation Chromatography (GPC) data were collected on Waters 2695, Wyatt Optilab rEx Refractometer, using Wyatt HELEOS II Multi-Angle Laser Light Scattering Detector. Empower and Astra software were used for data analysis. Two PL HFIP gel columns were used operated at 40° C., and HFIP with 0.01 M LiBr (0.2% H2O) as a mobile phase. Flow rate was 0.7 mL/min with injection volume of 70 μL. Solution concentration was approximately 2 mg/mL. Weight average molecular weight (Mw) obtained from GPC measurements can be expressed interchangeably, in both, Daltons or g/mol units.

The Nuclear Magnetic Resonance, NMR method identifies and determines the chemical composition of inventive and non-inventive formulations using proton nuclear magnetic resonance ($^1HNMR$) spectroscopy. The instrument used was the 400 MHz (9.4 Tesla) Varian UnityNOVA NMR Spectrometer; an appropriate deuterated solvent, such as Hexafluoroacetone sesquideuterate (HFAD) of at least 99.5% purity D (ETHICON ID #2881, CAS 10057-27-9) was used. Sample preparation: In triplicate, 6-10 mg of each sample was weighted and placed into separate 5 mm NMR tubes. Under nitrogen gas in a glove box, 300+/−10 μL of HFAD was added using 1000 μL syringe, to each NMR tube and cap.

Meanwhile, a solvent blank was prepared. The samples were then removed from the nitrogen glove bag/box and NMR tube(s) were placed in a sonic bath, and sonicated until the sample was dissolved, and no evidence of solid polymer existed. Subjecting the samples again under the nitrogen flow, 300+/−10 μL benzene-d6 was added using a 1000 μL syringe to each NMR tube and capped. The tubes were shake well to ensure uniform mixing of the HFAD and benzene-d6 solvents.

Mechanical properties of the fibers and braids before and after hydrolysis treatment, such as straight tensile (using uninterrupted, continues straight piece of a fiber or braid) and knot tensile strength (one simple knot introduced in the middle of a fiber or braid) were measured by an Instron tester. The Instron model was ID #TJ-41, equipped with 100-lb load cell LC-147 with pneumatic grips at clamping pressure around 60 psi. The Instron Gauge speed was one inch per minute with the Gauge length of one inch. A 100 lb. load cell was used. For the time zero, steel faces were used on the Instron machine, for all other hydrolysis times rubber faces were used to avoid slippage. The fiber diameters were measured using Federal gauge (Products Corp. Providence, R.I.) model #57B-1, identification #W-10761.

In vitro BSR measurements were conducted at physiologically relevant in vitro conditions: 7.27 pH phosphate buffered saline solution with molarity of 0.01M (IX) maintained at 37° C. temperature. Two Haake water baths equipped with a ThermoScientific DC 10 motor (Model W46, equipment ID: BT-029) were used. The data for BSR evaluations were given in pounds and percentages. At specified time points, the tensile strength of samples was tested using an Instron material testing machine. The test parameters were 1 inch gauge length and 1 inch per minute crosshead speed.

In vivo tissue reaction and total absorption study for the invented EO sterilized braids were conducted at an outside facility following a GLP protocol and all applicable ISO standards. A total of 68 rats were implanted in the gluteal muscles (two sites per side) with one of the two test articles on one side and control articles (sterile braids made from random 90/10 Gly/Lac copolymer) on the other. A total of 31 rats were implanted with the size 2/0 sterile braids and 37 rats with the size 2 sterile braids of the polymers of Ex. 15. For the total absorption study, six animals of each of these groups were euthanized at 14, 56, 77, and 119 days. At the indicated interval, animals were euthanized and implantation sites were collected for histological processing and microscopic evaluation.

In order to follow conversion of monomers (lactide and glycolide) in real polymerization time, a FT-NIR spectrometer [Antaris II Fourier Transform Near Infrared Spectrometer, supplied by ThermoFischer Scientific] equipped with a ¼" diameter transmission probe and 2-meter optical cable was used. The measurements were conducted during both stages of the process. TQ Analyst Software was used to analyze real-time NIR spectra. The overall scanning (collection) time was set to 64 scans, with 4 $cm^{-1}$ spectral resolution. Exactly every two minutes the spectra were collected as a function of reaction time. The area under the carbonyl peak (the first harmonic overtone of a combination band), located at about 4,800 $cm^{-1}$ was used to monitor glycolide conversion. For lactide conversion, the first overtone stretching vibration of methyl group, located at about 5,700 $cm^{-1}$ was used for monitoring purposes. An NIR transmission probe (supplied by Axiom) was placed in the lower part of the vessel, where a thermocouple measuring the batch temperature sits.

The following examples are illustrative of the principles and practice of the present invention, although not limited thereto. Numerous additional embodiments within the scope and spirit of the invention will become apparent to those skilled in the art once having the benefit of this disclosure.

Example 1 (Inventive)

Synthesis of a Segmented A-B-A Block Copolymer of Poly(Glycolide-co-L(−)-lactide) at an Overall 90/10 Glycolide/Lactide Molar Composition and a B-segment Molar Composition of 50/50 Glycolide/Lactide, Using Difunctional Initiator Using a 2.5-gallon cone vertical (CV) stainless steel oil-jacketed reactor equipped with corotating agitation, 684 grams of glycolide and 849 grams of L(−)-lactide were added along with 10.18 ml of diethylene glycol and 1.19 ml of a 0.33M solution of stannous octoate in toluene. After the initial charge, a vacuum/nitrogen purging cycle with agitation at a rotational speed of 5 RPM (reactor dependent) in an upward direction was initiated; the reactor was evacuated to pressures less than 250 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was kept at 5 RPM in an upward direction. The vessel was heated by setting the oil temperature controller to 185° C. When the batch temperature reached 110° C., rotation of the agitator was switched to a forward direction. The reaction continued for 2.5 hours from the time the batch temperature reached 180° C.

After the completion of the first stage portion of the polymerization, a very small amount of resin was discharged for analysis purposes; selected characterization was performed. The chemical composition of the prepolymer, as determined by NMR, was 50 mole percent polymerized lactide and 50 mole percent polymerized glycolide with 2.3 mole percent unreacted monomer. The DSC data revealed that the prepolymer was fully amorphous with no crystallinity developed even after heat treatment. The prepolymer exhibited an IV of 0.51 dL/g, and a weight average molecular weight (Mw) of 18,600 Daltons.

In the second stage portion of the polymerization, the heating oil controller set point was raised to 230° C., and 5,468 grams of molten glycolide monomer was added from a melt tank with an agitator speed of 15 RPM in a downward direction for 30 minutes. The agitator speed was then reduced to 7 RPM in the downward direction. The reaction proceeded for 1.5 hours from the time of the second glycolide addition, constituting the end of the final reaction period.

At the end of the final reaction period, the agitator speed was maintained at 7 RPM in the downward direction, and the polymer was discharged from the vessel into suitable containers. Upon cooling, the polymer was removed from the containers and placed into a freezer set at approximately −20° C. for a minimum of 12 hours. The polymer was then removed from the freezer and placed into a Cumberland granulator fitted with a sizing screen to reduce the polymer granules to approximately 3/16 inches in size. The granules were sieved to remove any "fines" and weighed. The net weight of the ground and sieved polymer was 5.25 kg. The ground polymer was then placed into a 3-cubic foot Patterson-Kelley tumble dryer to help remove residual monomer.

Once charged with the ground polymer, the Patterson-Kelley tumble dryer was closed, a dryer rotational speed of 4 RPM was initiated, and the pressure was reduced to less than 200 mTorr. These conditions were maintained with no heat for 18 hours. After the 18-hour period, the oil jacket temperature was set to 140° C. and maintained for 24 hours. At the end of the 24-hour heating period, the batch was allowed to cool for a period of 2 hours while maintaining rotation and vacuum. After cooling, the polymer was discharged from the dryer by pressurizing the vessel with nitrogen, opening the discharge valve, and allowing the polymer granules to descend into waiting vessels for long-term storage.

The long-term storage vessels were air tight and outfitted with valves allowing for evacuation so that the resin was stored under vacuum. The dried resin exhibited an IV of 1.35 dL/g, and a Mw of 67,800 Daltons. NMR analysis confirmed that the resin contained 90 mole percent polymerized glycolide and 10 mole percent polymerized L(−)-lactide, with a residual monomer content of 0.4 mole percent. The glass transition temperature (Tg) of the dried resin was 52° C., the melting point (Tm) was 215° C., and the heat of fusion (ΔHm), was 70.9 J/g as determined by DSC using the first heat scan. Wide Angle X-Ray Diffraction (WAXD) data on the dried sample revealed 42% crystallinity.

Example 2 (Non-Inventive/Comparative)

Synthesis of a Segmented A-B Block Copolymer of Poly(Glycolide-co-L(−)-lactide) at an Overall 90/10 Glycolide/Lactide Molar Composition and a B-Segment Molar Composition of 50/50 Glycolide/Lactide, Using Monofunctional Initiator In this Example, dodecanol as a monofunctional initiator was used (as in the prior art U.S. Pat. No. 6,007,565) instead of diethylene glycol (difunctional initiator).

Using a 2.5-gallon cone vertical (CV) stainless steel oil-jacketed reactor equipped with corotating agitation, 684 grams of glycolide and 849 grams of L(−)-lactide were added along with 24.0 ml of dodecanol (DD) and 1.19 ml of a 0.33M solution of stannous octoate in toluene. After the initial charge, a vacuum/nitrogen purging cycle with agitation at a rotational speed of 5 RPM in an upward direction was initiated. The reactor was evacuated to pressures less than 250 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was kept at 5 RPM in an upward direction. The vessel was heated by setting the oil controller at 185° C. When the batch temperature reached 110° C., rotation of the agitator was switched to a downward direction. The reaction continued for 2.5 hours from the time the batch temperature reached 180° C., constituting the end of the first stage polymerization.

After the completion of the first stage portion of the polymerization, a very small amount of resin was discharged for analysis purposes and selected characterization was performed. The chemical composition of the prepolymer, as determined by NMR, was 50 mole percent polymerized lactide and 50 mole percent polymerized glycolide with 2.1 mole percent of unreacted monomer. The DSC data revealed that the prepolymer was fully amorphous with no crystallinity developed even after heat treatment. The prepolymer (B-segment) exhibited an inherent viscosity of 0.61 dL/g and a Mw of 23,500 Daltons.

In the second stage portion of the polymerization, the heating oil controller set point was raised to 230° C. and 5,468 grams of molten glycolide monomer was added from a melt tank with the agitator speed of 15 RPM in an upward direction for 30 minutes. The agitator speed was then reduced to 7 RPM in the downward direction. The reaction proceeded for 1.5 hours from the time of the second glycolide addition, constituting the end of the final reaction period.

At the end of the final reaction period, the agitator speed was maintained at 7 RPM in the downward direction, and the polymer was discharged from the vessel into suitable containers. Upon cooling, the polymer was removed from the containers and placed into a freezer set at approximately −20° C. for a minimum of 12 hours. The polymer was then removed from the freezer and placed into a Cumberland granulator fitted with a sizing screen to reduce the polymer granules to approximately 3/16 inches in size. The granules were sieved to remove any "fines" and weighed. The net weight of the ground and sieved polymer was 4.72 kg. The ground polymer was then placed into a 3-cubic foot Patterson-Kelley tumble dryer to help remove residual monomer.

Once charged with the ground polymer, the Patterson-Kelley tumble dryer was closed, a dryer rotational speed of 3 RPM was initiated, and the pressure was reduced to less than 200 mTorr. These conditions were maintained with no heat for 18 hours. After the 18-hour period, the oil jacket temperature was set to 140° C. and maintained for 24 hours. At the end of the 24-hour heating period, the batch was allowed to cool for a period of 2 hours while maintaining rotation and vacuum. After cooling, the polymer was discharged from the dryer by pressurizing the vessel with nitrogen, opening the discharge valve, and allowing the polymer granules to descend into waiting vessels for long term storage.

The long-term storage vessels were air tight and outfitted with valves allowing for evacuation so that the resin was stored under vacuum. The dried resin exhibited an inherent viscosity of 1.35 dL/g, and a Mw of 66,200 Daltons. NMR analysis confirmed that the resin contained 90 mole percent polymerized glycolide and 10 mole percent polymerized L(−)-lactide, with a residual monomer content of 1.9 mole percent. The Tg, of the dried resin was 47° C., the Tm was 218° C., and the ΔHm was 74.7 J/g as determined by the DSC first heat scan.

Impact of Initiator Type on Resin Properties

Since DEG is used in Example 1, the resulting copolymer has an A-B-A chain sequence as presented before. If a monofunctional initiator is used, such as DD, the chain sequence would be of the form A-B. To evaluate the impact of this structural change on suture performance, a resin was made as described in Example 2 in which DD was used as the initiator instead of DEG, both having an overall target composition of 90/10 glycolide/lactide and a target B-segment composition of 50/50 glycolide/lactide.

A comparison of the copolymer properties between Example 1 and Example 2 is summarized in the Table 1.

TABLE 1

Polymer Properties of DEG and DD Initiated Polymers from Example 1 and Example 2, Respectively

|  |  | Example 1 (DEG-Initiated) | Example 2 (DD-Initiated) |
|---|---|---|---|
| Prepolymer (B-Segment) | Mw (g/mol) | 18,607 | 23,500 |
|  | IV (dL/g) | 0.51 | 0.61 |
|  | Unreacted Monomer (mol %) | 2.3 | 2.1 |
| Dried Polymer | Mw (g/mol) | 67,800 | 66,200 |
|  | IV (dL/g) | 1.35 | 1.35 |
|  | Polymerized Glycolide (mol %) | 89.9 | 88.3 |
|  | Unreacted Glycolide Monomer (mol %) | 0.3 | 1.6 |
|  | Polymerized Lactide (mol %) | 9.7 | 9.8 |
|  | Unreacted Lactide Monomer (mol %) | 0.1 | 0.3 |
|  | Tm (° C.) | 215 | 218 |
|  | Tg (° C.) | 52 | 47 |
|  | $AC_L SL$ | 2.4 | 2.7 |

The two polymers were similar in terms of their final Mw, IV, prepolymer composition, and final polymer composition. However, the prepolymer IV of the DD batch was higher than that of the DEG batch, which is also supported by the higher Mw results. However, the monomer to initiator ratio (IR) was 614:1 and 457:1 for Example 1 and Example 2, respectively, resulting in practically identical final copolymer IV and Mw.

The Tm was also higher for the DD batch. This is because the polymerized glycolide block (A-segment) for the A-B type polymer (DD initiated) will be almost twice as long as the polymerized glycolide end segments in the A-B-A type polymer (DEG initiated). Since the glycolide A-segment is much longer for the DD-initiated A-B type polymer, the polymer system will tend to behave closer to a polyglycolide homopolymer, which has a melting point of about 224° C.

Both of these copolymers were extruded into 56 denier yarn and braided into size 2/0 suture. The extrusion and braiding details are given in Example 13.

Examples 3-12 (Inventive and Non-Inventive)

Synthesis of Segmented A-B-A Block Copolymers of Poly (Glycolide-Co-L(−)-Lactide) at an Overall 90/10 Glycolide/Lactide Molar Composition Having Different B-Segment Molar Compositions, all Using Difunctional Initiator The synthesis procedure as described in Example 1 was repeated in a 2.5-Gallon cone vertical (CV) reactor using difunctional initiator (DEG), at an initiator ratio (moles of monomer:moles of initiator) of 550:1, but varying the B-segment (prepolymer) monomer composition, while keeping the final molar composition of 90/10 glycolide/lactide constant. The same catalyst (stannous octoate) and catalyst ratio (moles of monomer:moles of catalyst) of 150,000:1 was used for all the trials. Table 2 lists the different B-segment target molar compositions of the various A-B-A block copolymers made by this approach.

TABLE 2

List of B-Segment Molar Compositions of the
A-B-A Block Copolymers Produced in Examples 3-12

| Example Number | B-Segment Monomer Feed Ratio in Mole Percent (glycolide/lactide) | Measured B-Segment Polymer Composition in Mole Percent* (glycolide/lactide) |
|---|---|---|
| Example 3 | 80/20 | 79.7/18.7 |
| Example 4 | 70/30 | 69.7/28.8 |
| Example 5 | 60/40 | 59.7/38.5 |
| Example 6 | 50/50 | 49.8/48.0 |
| Example 7 | 40/60 | 39.8/56.2 |
| Example 8 | 30/70 | 30.2/66.3 |
| Example 9 | 20/80 | 20.6/75.5 |
| Example 10 | 15/85 | 15.7/79.3 |
| Example 11 | 10/90 | 11.4/83.9 |
| Example 12 | 5/95 | 6.0/84.9 |

*Does not include unreacted monomer.

Overall Copolymer Composition Summary:

The A-B-A copolymers at the end of the polymerization (discharged resin), and after the drying step were characterized. The NMR results demonstrated that the overall copolymer compositions at the discharge and after drying were consistent across all runs as shown in Table 3.

TABLE 3

Average Overall Polymer Composition of the Discharged Polymer
and of the Dried Polymer from Examples 3-12 by NMR

| | Average (mole %) | Standard Deviation |
|---|---|---|
| Discharged Polymer | | |
| Polymerized Glycolide | 89.3 | 0.4 |
| Unreacted Glycolide Monomer | 1.1 | 0.4 |
| Polymerized Lactide | 9.4 | 0.4 |
| Unreacted Lactide Monomer | 0.2 | 0.0 |
| Dried Polymer | | |
| Polymerized Glycolide | 89.8 | 0.6 |
| Unreacted Glycolide Monomer | 0.6 | 0.4 |
| Polymerized Lactide | 9.5 | 0.3 |
| Unreacted Lactide Monomer | 0.2 | 0.1 |

Mw and IV Summary:

The copolymer resins produced from Examples 3-12 were analyzed for Mw and IV. The Mw ranged from 57,000 to 74,200 g/mol at reactor discharge, and from 54,200 to 72,500 g/mol after drying. This aligned with the spread of IV generated, which ranged from 1.22 to 1.53 dL/g for the dried copolymers. FIG. 1 and FIG. 2 summarize the Mw and IV results for these polymer samples respectively.

Sequence Distribution Summary:

In order to characterize the sequence distribution of the resulting copolymers, the Average Chain Sequence Length (ACSL) of the lactoyl moiety $\{-OCH(CH_3)C=O-\}$ was assessed using NMR. It's known that polymerized lactide monomer is composed of two lactoyls in series that are relatively stable. Therefore, the lactoyl ACSL ($AC_LSL$) for a random 90 G/10 L copolymer is expected to be close to 2. As conventionally calculated by the Harwood run number [ACSL=1+x/y], the $AC_LSL$ is predicted to equal 1.11 for the random copolymer [1+10/90=1.11]. However, because the polymerized lactide repeat unit does not typically split, transesterification of adjoining lactoyls are usually not observed. Therefore, the $AC_LSL$ of a fully randomized 90/10 glycolide/lactide copolymer, where the lactoyl repeat unit is $(-OCH(CH_3)C=O-)_n$, would be 2.11 [2+x/y=2.11].

For the copolymers of Example 1, and Examples 3-12, since all the lactide is contained in the center segment of the A-B-A polymer chain (B-segment), the $AC_LSL$ of the A-B-A polymer is expected to increase as the lactide content in the B-segment composition is increased. A plot of the $AC_LSL$ results of the A-B-A polymer are shown in FIG. 3 and are aligned to the previously stated expectation, in which the $AC_LSL$ increased from 2 when as the percent lactide in the B-segment is increased.

Example 13

Extrusion and Braiding of the Copolymers Described in Examples 1-12
Extrusion and Orientation Apparatus and Conditions The copolymers described in Examples 1-12 were extruded into multiple filament strands through a 1-inch conventional vertical extruder. The extruded multifilament strands were collected on a take-up winder and then drawn on a conventional drawing stand. Typical processing conditions are provided in Table 4.

TABLE 4

Extrusion and Orientation Conditions

| Extrusion Components | Range of Variables |
|---|---|
| Extruder Feed Zone Temp. (° C.) | 165-205 |
| Extruder Transition Zone Temp. (° C.) | 185-225 |
| Extruder Metering Zone Temp. (° C.) | 190-245 |
| Extruder Barrel Pressure (psi) | 1200 (±300) |
| Metering Pump Temp. (° C.) | 185-255 |
| Pump Outlet Pressure (psi) | 1500-5000 |
| Extrusion Block Temp. (° C.) | 185-255 |
| Spinneret Temp. (° C.) | 205-265 |
| Heated Sleeve/Chimney Temp (° C.) | 235-310 |
| Distance from Die to 1st Take-Up Godet | About 17 feet |
| Take-up Winder Speed (fpm) | 1732 (+/−20) |
| Orientation Conditions | Operating Range |
| Orientation Roll Temperature (C) | 75-95 |
| Drawing Roll Temperature (C) | 95-135 |
| Let-off Roll Temperature (° C.) | Ambient |
| Orientation Roll Speed (fpm) | 200 (+/−7) |
| Drawing Roll Speed (fpm) | 998 (+/−10) |
| Let-off Roll Speed (fpm) | 1000 (+/−10) |
| Total Draw Ratio | about 5.0 |
| Drawn Denier Per Filament (DPF) | about 2.0 |
| Total Drawn Yarn Denier | 10-100 |

Note that the drawn fiber size is preferably kept constant at about 2.0 denier per filament (dpf) using a fixed total draw ratio of around 5.0. Based on the suture size and total yarn denier needed, the number of spinneret holes, metering pump size and speed may be varied. For example, to make size 2-0 suture with 56-denier yarn, a spinneret of 28 holes would be used with a ½ size pump having a throughput of about 0.30 cc/rev at a speed of about 41 rpm. Depending on the polymer molecular weight, IV or melt index, the temperatures of the extrusion and/or orientation may be varied or optimized to achieve desirable optimum fiber properties within the ranges recommended in Table 4 above.

Braiding Conditions

To produce braided suture material, yarns were first bobbin wound and braided using a 16-carrier/3 core construction on a New England Butt braider. After braiding, the material was skeined and solvent scoured in ethyl acetate to remove lubricant finishes and foreign materials accumulated during upstream manufacturing steps. Using dedicated equipment, all skeins were skein-scoured in an opened-top for 15 minutes, and drip-dried. After scouring, the skeins were then re-spooled for subsequent hot stretching. During the hot stretching process, the suture material was drawn on heated rolls in order to mechanically align the core and sheath yarns of the braid. For the size 2-0 suture produced, a draw ratio of 14% was used. After hot stretching, the suture material was rack annealed in an inert gas annealing oven for 6 hours at a temperature of 124° C.

Example 14

Physical Properties of the Braids Produced and Described in Example 13
Impact of Initiator Type on Braid Physical Properties, Including BSR The copolymers of Examples 1 and 2 were extruded into 56d yarn and braided into size 2/0 suture as described in Example 13. The results are summarized in Table 5.

TABLE 5

Tensile Strength and BSR Results of 2-0 Braids Made from DEG and DD Initiated Copolymers of Examples 1 and 2

| Polymer Example No. | Initiator Type | Knot Tensile (lbs.) | Straight Tensile (lbs.) | 35 Day % BSR | 42 Day % BSR |
| --- | --- | --- | --- | --- | --- |
| 1 | DEG | 9.83 | 17.6 | 58.3 | 26.7 |
| 2 | DD | 9.52 | 17.9 | 32.0 | 9.4 |

Although the initial knot tensile and straight tensile strengths are similar between the braids constructed from DEG and DD initiated polymers of Examples 1 and 2, the most unexpected and surprising result observed was the significant impact of initiator type on BSR performance. The braid constructed from DD-initiated polymer of Example 2 exhibited significantly shorter BSR performance than the braid constructed from the DEG-initiated polymer of Example 1. This clearly demonstrated the critical importance of using a difunctional initiator to produce A-B-A types of 90/10 glycolide/lactide copolymers for use in suture systems that require extended BSR properties.

B-Segment Compositional Assessment on Braid Physical Properties

To explore the impact of B-segment composition on suture performance, a series of A-B-A type copolymers were produced with different B-segment compositions, as described in Examples 3-12. The explored B-segment compositions ranged from 20 mole % to 95 mole % lactide. Their extrusion, braiding and post-processing steps were presented in Example 13. Table 6 summarizes the various A-B-A copolymers that were produced along with their resulting size 2-0 suture knot tensile, straight tensile, and BSR results. In addition, FIG. 4 and FIG. 5 that provide the BSR performance and straight tensile strength of the suture versus B-segment composition, respectively.

TABLE 6

Size 2-0 Suture Performance Made from the A-B-A Copolymers with Various B-Segment Compositions of Examples 3-12

| Example No. | B-Segment Composition (Glycolide/Lactide) (Mole %) | Knot Tensile (lbs.) | Straight Tensile (lbs.) | 35 Day % BSR | 42 Day % BSR |
| --- | --- | --- | --- | --- | --- |
| 12 | 5/95 | 9.78 | 17.09 | 29.5 | 4.7 |
| 11 | 10/90 | 9.78 | 16.57 | 31.5 | 4.9 |
| 10 | 15/85 | 9.68 | 16.27 | 32.7 | 0.0 |
| 9 | 20/80 | 10.13 | 17.14 | 43.5 | 13.2 |
| 8 | 30/70 | 9.65 | 17.61 | 48.4 | 18.9 |
| 7 | 40/60 | 9.65 | 17.34 | 51.6 | 26.8 |
| 6 | 50/50 | 9.83 | 17.57 | 58.3 | 26.7 |
| 5 | 60/40 | 9.89 | 16.52 | 50.5 | 20.6 |
| 4 | 70/30 | 9.62 | 16.05 | 35.1 | 8.0 |
| 3 | 80/20 | 9.93 | 19.02 | 24.4 | 6.3 |

Surprisingly, the suture braid constructed from the A-B-A copolymer that had a B-segment molar composition of 50/50 glycolide/lactide (Example 6) produced the best 35-day BSR performance. Also, the samples produced from B-segment molar compositions of 50/50 (Example 6) and 40/60 glycolide/lactide (Example 7) exhibited the best 42-day BSR performance, both yielding % BSR of around 27%. This is a very important discovery, paving the way for the optimal chemical architecture of a B-segment composition of 50-60 mole percent of lactide in the overall A-B-A copolymer. The initial straight and knot tensile strengths of the sutures of these examples were not significantly impacted by changing the composition of the B-segment. Therefore, a target B-segment molar composition of 50/50 glycolide/lactide was identified as an optimal for the A-B-A type copolymers having an overall molar composition of 90/10 glycolide/lactide, as they yield materials that could be very useful for suture applications requiring extended BSR.

Example 15 (Inventive)

Large-Scale Synthesis of a Segmented A-B-A Block Copolymer of Poly(Glycolide-co-L(−)-lactide) at an Overall 90/10 Glycolide/Lactide Molar Composition and a B-Segment Molar Composition of 50/50 Glycolide/Lactide, Using Difunctional Initiator This example describes the inventive synthesis of a segmented A-B-A block copolymer with an overall target molar composition of 90/10 glycolide/lactide and a target B-segment molar composition of 50/50 glycolide/lactide, in the larger-scale 15-gallon Benco-style reactor with critical fast agitation at the start of the second stage, low catalyst ratio of 150 k:1, initiator ratio of 750:1, and a pelletization process for the discharge. Throughout the polymerization, monomer conversion was monitored in real-time by remote FT-NIR spectroscopy (Antaris II, Thermo) using a ¼" NIR transmission probe (supplied by Axiom).

Using a large-scale 15-gallon stainless steel Benco reactor equipped with an oil jacket and agitation, 6,347 grams of glycolide and 7,881 grams of L(−)-lactide were added along with 77.4 grams of difunctional initiator (DEG), 11.05 ml of a 0.33M solution of stannous octoate in toluene, and 130 grams of D&C Violet Number 2 dye. After the initial charge, a vacuum/nitrogen purging cycle with agitation at a rotational speed of 10 RPM in an upward direction for 20 minutes was initiated. The reactor was evacuated to pressures less than 200 mTorr followed by the introduction of nitrogen gas. The cycle was repeated once again to ensure a dry atmosphere. At the end of the final nitrogen purge, the pressure was adjusted to be slightly above one atmosphere and the oil temperature controller was set to 185° C., while the rotational speed of the agitator was maintained at 10 RPM in an upward direction. After 45 minutes of heating, the rotation of the agitator was switched to a downward direction. The reaction continued for about 3 hours from the time the agitator rotation was switched to forward direction, constituting the end of the first polymerization stage.

After the completion of the first stage portion of the polymerization, a very small amount of the prepolymer resin (B-segment) was discharged for analysis purposes and characterization was performed. The chemical composition of the prepolymer, as determined by NMR, was 50 mole percent polymerized glycolide and 50 mole percent polymerized lactide with about 2 mole percent of unreacted monomer remaining, consisting mostly of lactide. The DSC data revealed that the prepolymer was fully amorphous with no crystallinity developed even after heat treatment. The prepolymer exhibited an IV of 0.60 dL/g, and a Mw of 24,700 Daltons.

In the second stage portion of the polymerization, the heating oil controller set point was raised to 215° C. and the agitator was set to 20 RPM in an upward direction, upon which an additional 50,773 grams of molten glycolide monomer was added from a melt tank. After 60 minutes from the second glycolide charge, the agitator speed was then reduced to 15 RPM in the forward direction and the oil temperature setting was reduced to 207° C. for the reminder of the run. The reaction proceeded for a total of 165 minutes from when the second glycolide addition was performed, constituting the end of the final stage reaction.

At the end of the final reaction period, the agitator speed was reduced to 4 RPM in the downward direction, and the polymer was discharged using the Gala underwater pelletizing apparatus. The die hole size was 0.093" with 4 holes opened. The die temperature was kept between 247 and 275° C. The pelletizer material output was about 118 kg/hr, yielding a net weight of 54.2 kg. Upon cooling, the pellets were placed in the freezer for storage until drying. The pellets were then placed into a 3-cubic foot Patterson-Kelley tumble dryer to help remove residual monomer. The drying procedure was carried out exactly as described in Examples 1 and 2.

The dried pellets exhibited an IV of 1.39 dL/g and a Mw of 71,200 Daltons. NMR analysis confirmed that the resin contained 90 mole percent polymerized glycolide and 10 mole percent polymerized L(−)-lactide, with a residual monomer content of 0.7 mole percent. The Tg of the dried resin was 50° C., the Tm was 216° C., and the ΔHm was 53.2 J/g as determined by DSC using the first heat scan. Wide Angle X-Ray Diffraction (WAXD) data on the dried sample revealed 38% crystallinity.

Example 16 (Inventive)

Large-Scale Synthesis of a Segmented A-B-A Block Copolymer of Poly(Glycolide-co-L(−)-lactide) at an Overall 90/10 Glycolide/Lactide Molar Composition and a B-Segment Molar Composition of 50/50 Glycolide/Lactide, Using Difunctional Initiator, and Dual Catalyst Addition This example describes the inventive synthesis of a segmented A-B-A block copolymer with an overall target molar composition of 90/10 glycolide/lactide and a target B-segment molar composition of 50/50 glycolide/lactide, in a 15-gallon reactor with an extra low catalyst level (catalyst ratio of 200 k:1), using a dual catalyst addition method in which a portion of catalyst is added at the start of first stage reaction, and a second portion of catalyst is added in early stages of the second stage polymerization. The use of this dual catalyst addition method allows for an ultra-low catalyst concentration to be employed. Throughout the polymerization, monomer conversion was monitored in real-time by remote FT-NIR spectroscopy (Antaris II, Thermo) using a ¼" NIR transmission probe (supplied by Axiom).

Using a large-scale 15-gallon stainless steel oil-jacketed Benco reactor equipped with agitation, 4,882 grams of glycolide and 6,062 grams of L(−)-lactide were added along with 59.5 grams of difunctional initiator (DEG), 2.12 ml of a 0.33M solution of stannous octoate in toluene, and 100 grams (0.2 weight percent) of D&C Violet Number 2 dye was added. After the initial charge, a vacuum/nitrogen purging cycle with agitation at a rotational speed of 10 RPM in an upward direction for 20 minutes was initiated. The reactor was evacuated to pressures less than 200 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was kept at 10 RPM in an upward direction and the vessel was heated by setting the oil controller at 185° C. After 30 minutes the rotation of the agitator was switched to a forward direction. The first stage reaction continued for about 5 hours, based on NIR measurements, to account for slower monomer conversion resulting from lower catalyst level in the first stage.

After the completion of the first stage portion of the polymerization, a very small amount of resin was discharged for analysis purposes and selected characterization was performed. The chemical composition of the prepolymer, as determined by NMR, was 50 mole percent polymerized glycolide and 50 mole percent polymerized lactide with about 2 mole percent of unreacted monomer, mostly lactide. The DSC data revealed that the prepolymer was fully amorphous with no crystallinity developed even after heat treatment. The prepolymer (B-segment) exhibited an inherent viscosity of 0.59 dL/g and a Mw of 24,300 Daltons. Wide Angle X-Ray Diffraction (WAXD) data on the dried sample revealed 41% crystallinity.

In the second stage portion of the polymerization, the heating oil controller set point was raised to 216° C. and the agitator speed and direction was set to 18 RPM upward, after which 38,656 grams of molten glycolide monomer was added from a melt tank. After 10 minutes from the second glycolide charge, the agitator direction was set to 18 RPM forward. After 30 minutes from the second glycolide charge, the second catalyst addition of 4.25 ml was conducted to achieve an overall catalyst ratio of 200 k:1. To ensure all of the catalyst in this second catalyst addition was captured, the 4.25 ml of catalyst was mixed with of 400 grams of glycolide in powder form before adding to the reactor. When the catalyst addition was complete, the oil temperature controller was set to 207° C. and the agitator RPM was reduced to 7.5 for the reminder of the run. The reaction proceeded for 165 minutes from the second glycolide charge prior to the discharge, constituting the end of the final reaction period.

At the end of the final reaction period, the agitator speed was maintained at 7.5 RPM in the downward direction, and the polymer was discharged from the vessel into suitable containers. Upon cooling, the polymer was placed into a freezer set at approximately −20° C. for a minimum of 12 hours. The polymer was then removed from the freezer and placed into a Cumberland granulator fitted with a sizing screen to reduce the polymer granules to approximately 3/16 inches in size. The granules were sieved to remove any "fines" and weighed. The net weight of the ground and sieved polymer was 42.4 kg and was then placed into a 3-cubic foot Patterson-Kelley tumble dryer to remove any residual monomer. The drying procedure was carried out exactly as described in Examples 1 and 2.

The dried pellets exhibited an IV of 1.46 dL/g and a Mw of 76,500 Daltons. NMR analysis confirmed that the resin contained 90 mole percent polymerized glycolide and 10 mole percent polymerized L(-)-lactide, with a residual monomer content of 0.6 mole percent. The Tg of the dried resin was 46° C., the Tm was 216° C., and the ΔHm was 67.8 J/g as determined by DSC using the first heat scan.

As mentioned previously, a FT-NIR spectrometer equipped with a ¼" diameter transmission probe and 2-meter optical cable was used to follow glycolide and lactide conversion in real polymerization time during both stages of the reaction. In FIG. 6A, the area under the glycolide and lactide peaks are plotted against the reaction time in the first polymerization stage for the batch made in this Example. In FIG. 6B, the area under the monomer peaks are converted into percentages and the conversion progress is graphically illustrated as a function of reaction time. An assumption was made, based on real-time FT-NIR monitoring, was that monomer conversion was sufficiently complete at the end of the first stage. Based on NMR results on the inventive prepolymers, glycolide generally converted to almost 100%, but about 1.5-2.0 mole percent of lactide monomer remained after the first stage. This unreacted lactide is available for polymerization in the second stage of the reaction, incorporating into the glycolide A-segments. Therefore, to maintain A-segments that are substantially comprised of glycolide, it is important to achieve as much lactide monomer conversion in the first stage as possible to minimize the available lactide in the second stage.

As FIGS. 6A and 6B indicate, the glycolide conversion in the first stage was very fast for Example 16, and after about 40-50 minutes appeared to reach the completion. On the other hand, the lactide polymerization rate was notably slower, especially in the later prepolymer stages, and took longer time to convert down to about 2 mole % of its original value.

Example 17 (Inventive)

Large-Scale Synthesis of a Segmented A-B-A Block Copolymer of Poly(Glycolide-co-L(-)-lactide) at an Overall 90/10 Glycolide/Lactide Molar Composition and a B-Segment Molar Composition of 50/50 Glycolide/Lactide, Using Difunctional Initiator, and Slow Agitation in the Second Stage This example describes the inventive synthesis of a segmented A-B-A block copolymer with an overall target molar composition of 90/10 glycolide/lactide and a target B-segment molar composition of 50/50 glycolide/lactide in a large-scale 15-gallon Benco reactor with a catalyst ratio of 150 k:1, with all catalyst added in the first stage as in Example 15, but with slower agitation at the beginning of the critical second stage reaction period. It will be shown that this method was not optimal in producing a resin that would result in sutures with longer BSR performance. Throughout the polymerization, monomer conversion was monitored in real-time by remote FT-NIR spectroscopy (Antaris II, Thermo) using a ¼" NIR transmission probe (supplied by Axiom).

Using a large-scale 15-gallon stainless steel oil-jacketed Benco reactor equipped with agitation, 4,882 grams of glycolide and 6,062 grams of L(-)-lactide were added along with 59.5 grams of difunctional initiator (DEG), 8.50 ml of a 0.33M solution of stannous octoate in toluene, and 100 grams of D&C Violet Number 2 dye. After the initial charge, a vacuum/nitrogen purging cycle with agitation of 10 RPM in an upward direction for 20 minutes was initiated. The reactor was evacuated to pressures less than 300 mTorr followed by the introduction of nitrogen gas. The cycle was repeated once again to ensure a dry atmosphere. At the end of the final nitrogen purge, the pressure was adjusted to be slightly above one atmosphere, while maintaining an agitator speed of 10 RPM in an upward direction. The vessel was heated by setting the oil controller at 185° C. After 30 minutes from initiating heat, the agitator was switched to a forward direction. The reaction continued for 3.5 hours from the time the oil temperature was set at 185° C.

After the completion of the first stage portion of the polymerization, a very small amount of resin was discharged for analytical purposes and selected characterization was performed. The chemical composition of the prepolymer, as determined by NMR, was 50 mole percent polymerized glycolide and 50 mole percent polymerized lactide with about 2 mole percent of residual unreacted monomer, mostly lactide. The DSC data revealed that the prepolymer was fully amorphous with no crystallinity developed even after heat treatment. The prepolymer (B-segment) exhibited an IV of 0.62 dL/g and a Mw of 25,900 Daltons.

In the second stage portion of the polymerization, the heating oil controller set point was raised to 216° C. while setting the agitator speed to 18 RPM upward, after which an additional 39,056 grams of molten glycolide monomer was added from a melt tank. After 10 minutes from the second glycolide addition, the agitator speed was changed to forward rotation. After 30 minutes from the second glycolide charge, the oil temperature was set to 207° C. After 60 minutes from the second glycolide charge, the agitation speed was reduced to 7.5 RPM for the reminder of the run. The reaction proceeded about 165 minutes from the second glycolide charge prior to the discharge, constituting the end of the final reaction period.

At the end of the final reaction period, the agitator speed was maintained at 7.5 RPM in the downward direction, and the polymer was discharged from the vessel into suitable containers. Upon cooling, the polymer was removed from the containers and placed into a freezer set at approximately -20° C. for storage for a minimum of 12 hours. The polymer was then removed from the freezer and placed into a Cumberland granulator fitted with a sizing screen to reduce the polymer granules to approximately ³⁄₁₆ inches in size. The granules were sieved to remove any "fines" and weighed. The net weight of the ground and sieved polymer was 35.3 kg, and this ground polymer was then placed into a 3-cubic foot Patterson-Kelley tumble dryer to remove residual monomer. The drying procedure was carried out exactly as described in Examples 1 and 2.

The dried pellets exhibited an IV of 1.39 dL/g and a Mw of 72,300 Daltons. NMR analysis confirmed that the resin contained 90 mole percent polymerized glycolide and 10 mole percent polymerized L(-)-lactide, with a residual monomer content of 1.8 mole percent. The Tg of the dried resin was 47° C., the Tm was 215° C., and the ΔHm was 63.1 J/g, as determined by DSC using the first heat scan.

Inadequate mixing efficiency for this batch was identified in real-processing time by the remote FT-NIR spectroscopy. In FIG. 7, the second stage glycolide conversion for the Example 17 batch was given as a function of the second stage polymerization time. Corresponding data on two previous inventive batches, Examples 15 and 16, are also included for a comparison.

As FIG. 7 indicates, it took a much longer time for glycolide monomer to convert for the Example 17 batch than expected based upon results obtained on previous batches (Examples 15 & 16). This is due to the difficulty of mixing the relatively low viscosity molten glycolide monomer from the melt tank with the relatively high viscosity prepolymer. Inadequate mixing would slow down the copolymerization rates and affect the physical properties of the resin. Several critical steps were implemented in this study that helped in solving this problem. These are: a) faster agitation speed; b) extending the mixing time, or the time in which a faster agitation speed and higher reactor temperature is applied; c) increased prepolymer batch temperature prior to the second glycolide addition; and/or, d) using the dual catalyst addition as successfully demonstrated in Example 16.

The dried resins of Examples 15-17 were extruded and braided into 2-0 size suture according to the procedures described in Example 13. The annealed braids were submitted for in vitro BSR testing, and the results are presented in Table 7.

TABLE 7

42-Day BSR Results for 2-0 Braids Made from Examples 15-17

| Example Number | 42 Day % BSR | Standard Deviation (%) |
|---|---|---|
| 15 | 42.6 | 0.1 |
| 16 | 40.2 | 4.3 |
| 17 | 24.6 | 6.5 |

It is evident from the data presented in Table 7 that inadequate mixing during the early stages of the second polymerization step of Example 17 negatively affected the 42-day BSR performance. On the other hand, the braids made from the polymer of Example 15 which used optimized mixing conditions, and the braids made from the polymer of Example 16 which used dual catalyst addition and ultra-low total catalyst level, generated significantly better 42-day BSR results. It should be noted that the 42-day BSR of 24.6% of Example 17 is still well above the 42-day BSR values achieved for the sutures made from the A-B type copolymers of Examples 19 and 20, which both yielded 42-day BSR values of <1%.

Example 18 (Inventive)

Large-Scale Synthesis of a Segmented A-B-A Block Copolymer of Poly(Glycolide-co-L(−)-lactide) at an Overall 90/10 Glycolide/Lactide Molar Composition and a B-Segment Molar Composition of 50/50 Glycolide/Lactide, Using High Catalyst Level The resin for this example was produced in the same manner as described in Example 15, except that a higher catalyst level was used. The catalyst ratio, as defined as "moles monomer:moles of catalyst" was decreased from 150 k:1 to 120 k:1. Note that since catalyst level is defined as "moles of monomer:moles of catalyst", a lower catalyst ratio corresponds to a higher catalyst level. For example, a catalyst ratio of 150 k:1 is equivalent to a catalyst level of 6.7 PPM, while a catalyst ratio of 120 k:1 is equivalent to a catalyst level of 8.3 PPM.

The dried pellets of Example 18 exhibited an IV of 1.32 dL/g and a $M_w$ of 67,800 Daltons. NMR analysis confirmed that the resin contained 90 mole percent polymerized glycolide and 10 mole percent polymerized L(−)-lactide, with a residual monomer content of 1.7 mole percent. The Tg of the dried resin was 48° C., the Tm was 214° C., and the ΔHm was 58.3 J/g as determined by DSC using the first heat scan.

Effect of Catalyst Level on BSR Properties

This example teaches that higher concentration of catalyst can negatively affect the properties of the final product. Higher catalyst concentration may lead to additional thermal degradation during the polymerization process and during downstream processing steps such as extrusion. On the other hand, lower levels of catalyst can lead to better thermal stability during polymerization and downstream processing, thus limiting the transesterifications and loss in molecular weight. The dried pellets from Example 18 were extruded and braided into two suture sizes using procedures described in Example 13. The annealed braids were submitted for in vitro BSR evaluation. In Table 8, the properties of the braid constructed from the copolymers of Example 18 and Example 15 are shown for a direct comparison.

TABLE 8

The Effect of Catalyst Level on Braid Properties of Braids Constructed from the Copolymers Described in Examples 15 and 18

| Example Number | Catalyst ratio (moles monomer: moles catalyst) | USP Size | Knot Tensile (lbs.) | Straight Tensile (lbs.) | 42 Day BSR (lbs.) | 42 Day % BSR |
|---|---|---|---|---|---|---|
| 15 | 150k:1 | 1 | 19.4 | 36.5 | 14.2 | 40.7 |
|  |  | 2-0 | 10.9 | 19.7 | 8.4 | 42.5 |
| 18 | 120k:1 | 1 | 17.3 | 35.0 | 7.9 | 23.7 |
|  |  | 2-0 | 9.3 | 17.5 | 4.3 | 24.0 |

As indicated in Table 8, initial tensile properties (straight and knot tensile) were slightly higher for the braids made from Example 15 (lower catalyst), but the in vitro BSR results were significantly better, both in pounds remaining and in percent BSR. The lower BSR results for the braids made from Example 18 could be the result of additional transesterification reactions, enabled by the increased catalyst level. This is a very similar case to Example 21, presented later in the text, where even higher catalyst level was used. As shown before, this resulted in randomization of the blocky structure and reduction in BSR performance. When comparing braids produced from the polymers of Example 15 and Example 18, the effect of catalyst level on BSR is clearly noticeable.

Example 19 (Non-Inventive and Comparative to Prior Art)

Synthesis of a Segmented A-B Block Copolymer of Poly (Glycolide-co-L(−)-lactide) at an Overall 90/10 Glycolide/ Lactide Molar Composition and a B-Segment Molar Composition of 55/45 Glycolide/Lactide, Using Monofunctional Initiator This example of a A-B block copolymer of poly(glycolide-co-L(−)-lactide) at an overall 90/10 glycolide/lactide molar composition [B-segment target molar composition of 55/45 glycolide/lactide] was made based on the teachings of U.S. Pat. No. 6,007,565 (Roby et al.) to demonstrate the criticality of using the procedures of the present invention for the desired long-BSR suture applications.

Using a 2.5-gallon stainless steel oil-jacketed CV reactor equipped with corotating agitation, 980 grams of glycolide and 980 grams of L(−)-lactide were added along with 4.72 ml of monofunctional initiator (DD) and 3.97 ml of a 0.33M solution of stannous octoate in toluene. The dye, D&C Violet Number 2 (14 grams), was added as well. After the initial charge, a vacuum/nitrogen purging cycle with agitation at a rotational speed of 5 RPM in an upward direction was initiated. The reactor was evacuated to pressures less than 150 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was kept at 5 RPM in an upward direction. The vessel was heated by setting the oil controller at 170° C. When the oil temperature reached 170° C., rotation of the agitator was switched to a downward direction. The reaction continued for 5.0 hours from the time the oil temperature reached 170° C.

After the completion of the first stage portion of the polymerization, a very small amount of resin was discharged for analytical purposes and selected characterization was performed. The chemical composition of the prepolymer, as determined by NMR, was 55 mole percent polymerized glycolide and 45 mole percent polymerized lactide with about 3 mole percent of residual unreacted monomer, mostly lactide. The DSC data revealed that the prepolymer was fully amorphous with no crystallinity developed even after heat treatment. The prepolymer (B-segment) exhibited an IV of 1.75 dL/g and a $M_w$ of 105,600 Daltons.

In the second stage of the polymerization 420 grams of glycolide was added to the reactor, and then the heating oil controller set point was raised to 220° C. When the oil temperature in the reactor reached 210° C., an additional 4,620 grams of molten glycolide monomer was added from a melt tank with the agitator speed of 25 RPM in an upward direction for 15 minutes. After 15 minutes, the agitator speed was then reduced to 20 RPM in the downward direction, and after another 15 minutes the agitator speed was further reduced to 15 RPM in a forward direction. After another 30 minutes the agitation was reduced to 7.5 RPM in a forward direction for the reminder of the run. The reaction proceeded 165 minutes from the last glycolide charge prior to the discharge, constituting the end of the final reaction period.

At the end of the final reaction period, the agitator speed was reduced to 4 RPM in the downward direction, and the polymer was discharged from the vessel into suitable containers. Upon cooling, the polymer was placed into a freezer set at approximately −20° C. for storage for a minimum of 12 hours. The polymer was then removed from the freezer and placed into a Cumberland granulator fitted with a sizing screen to reduce the polymer granules to approximately 3/16 inches in size. The granules were sieved to remove any "fines" and weighed. The net weight of the ground and sieved polymer was 4.80 kg; the ground polymer was then placed into a 3-cubic foot Patterson-Kelley tumble dryer to remove any residual monomer. The drying procedure was carried out exactly as described in Examples 1 and 2.

The dried resin exhibited an IV of 1.41 dL/g and a $M_w$ of 76,100 Daltons. NMR analysis confirmed that the resin contained 90 mole percent polymerized glycolide and 10 mole percent polymerized L(−)-lactide, with a residual monomer content of 0.3 mole percent. The Tg of the dried resin was 46° C., the Tm was 219° C., and the ΔHm was 63.6 J/g as determined by DSC using the first heat scan.

Example 20 (Non-Inventive and Comparative Example to Prior Art)

Synthesis of a Segmented A-B Block Copolymer Poly (Glycolide-co-L(−)-lactide) at an Overall 90/10 Glycolide/Lactide Molar Composition and a B-Segment Molar Composition of 55/45 Glycolide/Lactide, Using Low Monofunctional Initiator Level and High Catalyst Level This example of an A-B block copolymer of poly(glycolide-co-L(−)-lactide) at an overall 90/10 glycolide/lactide molar composition [B-segment target molar composition of 55/45 glycolide/lactide] was made in the similar fashion as Example 19, based on the teachings of U.S. Pat. No. 6,007,565, but this time the resin was made without dye, and with an initiator ratio (moles monomer:moles initiator) of 1,400:1, instead of 2,800:1.

The dried resin made by this method exhibited an IV of 1.62 dL/g and a Mw of 88,000 Daltons. NMR analysis confirmed that the resin contained 89 mole percent polymerized glycolide and 11 mole percent polymerized L(−)-lactide, with a residual monomer content of 0.3 mole percent. The Tg of the dried resin was 47° C., the Tm was 214° C., and the ΔHm was 61.6 J/g as determined by DSC using the first heat scan.

Example 21 (Non-Inventive and Comparative Example to Prior Art)

Synthesis of a Segmented A-B-A Block Copolymer of Poly(Glycolide-co-L(−)-lactide) at an Overall 90/10 Glycolide/Lactide Molar Composition and a B-Segment Molar Composition of 50/50 Glycolide/Lactide, Using Very High Catalyst Level This example of a A-B-A block copolymer of poly (Glycolide-co-L(−)-lactide) at an overall 90/10 glycolide/lactide molar composition [B-segment target molar composition of 50/50 Glycolide/Lactide] was made based on the teachings of the current invention, except for the high catalyst concentration suggested by U.S. Pat. No. 6,007,565 (Roby et al.).

Using a large-scale 15-gallon stainless steel oil-jacketed Benco reactor equipped with agitation, 6,347 grams of glycolide and 7,881 grams of L(−)-lactide were added along with 64.5 grams of difunctional initiator (DEG) and 36.82 ml of a 0.33M solution of stannous octoate in toluene. The dye, D&C Violet Number 2 (130 grams) was added in the mixture as well. After the initial charge, a vacuum/nitrogen purging cycle with agitation at a rotational speed of 10 RPM in an upward direction for 20 minutes was initiated. The reactor was evacuated to pressures less than 250 mTorr followed by the introduction of nitrogen gas. The cycle was repeated once again to ensure a dry atmosphere. At the end of the final nitrogen purge, the pressure was adjusted to be slightly above one atmosphere and the rotational speed of the agitator was maintained at 10 RPM in an upward direction. The vessel was heated by setting the oil controller at 185° C. After 45 minutes from initiating the heat, the rotation of the agitator was switched to a downward direction. The reaction continued for about 3.5 hours from the time the heat was initiated.

After the completion of the first stage portion of the polymerization, a very small amount of resin was discharged for analytical purposes; selected characterization was performed. The chemical composition of the prepolymer, as determined by NMR, was 50 mole percent polymerized glycolide and 50 mole percent polymerized lactide with about 2 mole percent of residual unreacted monomer, mostly lactide. The DSC data revealed that the prepolymer was fully amorphous with no crystallinity developed even after heat treatment. The prepolymer (B-segment) exhibited an IV of 0.70 dL/g and a $M_w$ of 28,800 Daltons.

In the second stage portion of the polymerization, the heating oil controller set point was raised to 215° C. and the agitator speed and direction was set to 20 RPM in an upward direction. Once the reactor temperature and agitation was set, 50,773 grams of molten glycolide monomer was added from a melt tank. After 10 minutes from the glycolide charge the agitator direction was switched to forward. After 30 minutes from the second glycolide charge, the oil temperature was set to 207° C. for the reminder of the run. The agitator speed was reduced further at 45 minutes, 90 minutes, 120 minutes, and 150 minutes from the glycolide addition to 15, 10, 7.5, and 6.0 RPM respectively. The reaction proceeded for 165 minutes from the second glycolide charge, constituting the end of the final reaction period.

At the end of the final reaction period, the agitator speed was reduced to 4 RPM in the downward direction, and the polymer was discharged using the Gala pelletizing apparatus. The die hole size was 0.093" with 4 holes opened. The die temperature was kept at 250° C. The speed of pelletization was 75 kg/hour, yielding 57.7 kg. Upon cooling, the pellets were placed in the freezer at −20° C. for storage for a minimum of 12 hours. After storage, the pellets were then placed into a 3-cubic foot Patterson-Kelley tumble dryer to remove any residual monomer. The drying procedure was carried out exactly as described in Examples 1 and 2.

The dried pellets exhibited an IV of 1.24 dL/g and a $M_w$ of 66,200 Daltons. NMR analysis confirmed that the resin contained 90 mole percent polymerized glycolide and 10 mole percent polymerized L(−)-lactide, with a residual monomer content of 0.8 mole percent. The Tg of the dried resin was 50° C., the Tm was 214° C., and the ΔHm was 56.0 J/g as determined by DSC using the first heat scan.

Example 22

Extrusion and Braiding of Prior-Art Resins Produced and Described in Examples 19, 20 and 21

Extrusion Conditions

The extrusion and orientation equipment apparatus used were the same as described in Example 13. Specific extrusion and orientation conditions and their major properties are given in Table 9A-B, and in Table 10, respectively for each of the extrudate spools and/or oriented fiber samples produced and tested. Detailed parameters used for the specific yarn samples are given for the prior art polymer samples of U.S. Pat. No. 6,007,565 as well as the best mode of this invention. Lube pump and godet speeds were maintained at 52 rpm, and 1732 fpm, respectively for each extrusion run.

Note that there are two types of extrusion conditions, "optimum" and "prior art", listed in Table 9A. The "optimum" refers to the optimized extrusion conditions that resulted in the highest mean yarn tenacity that we could achieve with a given polymer. The "prior art" refers to the extrusion conditions that were set using our vertical extruder as close as possible to that taught by the prior art, i.e., U.S. Pat. No. 6,007,565. The extruder barrel pressure was set at 1200 psi, with an observed range of about 1100 to 1300 psi. The observed pump pressure was in the range of about 2200 to about 3000 psi. The extruder screw speed ranged from about 16 to 28 RPM and the melt pump from about 41 to about 47 RPM.

TABLE 9A

Extrusion Conditions of Prior Art Resins Produced and Described in Examples 19, 20 and 21, as well as Conditions of the Present Invention of the Resin Described in Example 15

| | Polymer Example No. | | | | | |
|---|---|---|---|---|---|---|
| | 15 (Inventive) | 19 | 20 | | 21 | |
| Extrusion Type | Optimum | Prior Art | Prior Art | Optimum | Prior Art | Optimum |
| Feed Zone (° C.) | 182 | 227 | 224 | 182 | 204-227 | 182 |
| Transition (° C.) | 210 | 227 | 250 | 210 | 210-227 | 210 |
| Metering (° C.) | 238 | 227-238 | 250 | 246 | 227 | 227 |
| Pump (° C.) | 249 | 226-246 | 250 | 254 | 215-227 | 227 |
| Block (° C.) | 249 | 238-246 | 250 | 254 | 223-227 | 227 |
| Spinneret (° C.) | 260 | 238-249 | 250 | 266 | 223-227 | 229 |
| Chimney (° C.) | 299-288 | 265 | 265 | 299 | 265-288 | 288 |

TABLE 9B

Orientation Conditions of Prior Art Resins Produced and Described in Examples 19, 20 and 21, as well as Conditions of the Present Invention of the Resin Described in Example 15

| | Polymer Example No. | | | | | |
|---|---|---|---|---|---|---|
| | 15 (Inventive) | 19 | 20 | | 21 | |
| Extrusion Type | Optimum | Prior Art | Prior Art | Optimum | Prior Art | Optimum |
| Orientation Roll Speed (fpm) | 200 | 200 | 200 | 200 | 200 | 200 |
| Drawing Roll Speed (fpm) | 998 | 1148 | 1148 | 998 | 1148 | 998 |
| Let-Off Roll Speed (fpm) | 1000 | 1128 | 1128 | 1000 | 1128 | 1000 |
| Orientation Roll Temp. (° C.) | 85 | 98-99 | 97-98 | 78-80 | 86-88 | 76 |
| Drawing Roll Temp. (° C.) | 120 | 125-132 | 130 | 115 | 115 | 115 |
| Total Draw Ratio | 5.00 | 5.64 | 5.64 | 5.00 | 5.64 | 5.00 |

TABLE 10

Mean Physical Properties of 90/10 Gly/Lac Yarns Produced from the Resins Described in Examples 19-21, as well as the Inventive Resin Described in Example 15

| | Polymer Example No. | | | | | |
|---|---|---|---|---|---|---|
| | 15 (Inventive) | 19 | 20 | | 21 | |
| Extrusion Type | Optimum | Prior Art | Prior Art | Optimum | Prior Art | Optimum |
| Yarn Denier Mean | 55.7 | 55.5 | 55.2 | 56.2 | 56.3 | 56.2 |
| Yarn Denier Stdev | 0.10 | 0.26 | 0.10 | 0.44 | 0.33 | 0.15 |
| Mean Tenacity (gpd) | 8.04 | 5.80 | 6.65 | 7.43 | 6.46 | 7.54 |
| Tenacity Stdev | 0.11 | 0.38 | 0.08 | 0.31 | 0.25 | 0.30 |
| Mean Elongation (%) | 22.2 | 20.1 | 20.0 | 22.4 | 18.9 | 22.8 |
| Elongation Stdev | 0.25 | 1.23 | 0.52 | 0.51 | 0.37 | 0.47 |

From Table 10, for a given polymer resin (Example 20 and 21), a higher yarn tenacity with higher elongation was observed for yarn made by optimized conditions, with a total draw ratio of about 5.0, compared to the yarn samples using prior art conditions, which had a total draw ratio of 5.64. Also, yarns produced from the inventive polymer of Example 15 showed significantly higher mean tenacities than the yarn produced from the non-inventive polymers of Examples 19, 20, and 21.

Braiding and Downstream Processing Summary

To produce braided suture material, yarns were first bobbin wound and braided using a 16-carrier, 3 core construction on a New England Butt braider. After braiding, material was skeined and solvent scoured in ethyl acetate to remove lubricant finishes and foreign materials accumulated during upstream manufacturing steps. Using dedicated equipment, all skeins were skein-scoured in a beaker for 15 minutes, and drip-dried. After scouring, the skeins were then re-spooled for subsequent hot stretching. The suture material was drawn on the heated roll hot stretch to mechanically align the core and sheath yarns. For the suture size 2-0 produced, a draw ratio of 14% was used. After hot stretching, suture material was rack annealed in an annealing oven for 6 hours at a temperature of 124° C.

Materials

To produce the size 2-0 braids described above, individual 56 denier yarn spools were selected from the population of yarn spools that generated the mean physical properties in Table 10. The physical properties of the specific yarn used to produce these 2-0 braids are outlined in Table 11.

TABLE 11

Physical Properties of the Individual 56 Denier Yarns Used to Produce Size 2-0 Braids

| Polymer ID | Extrusion Conditions | Tenacity (gpd) | % Elongation |
|---|---|---|---|
| Example 15 | Optimized | 7.82 | 22 |
| Example 19 | Prior art | 6.28 | 19 |
| Example 20 | Optimized | 7.29 | 22 |
|  | Prior art | 6.73 | 20 |
| Example 21 | Optimized | 7.67 | 23 |
|  | Prior art | 6.79 | 19 |
|  | Prior art | 6.73 | 20 |

From Table 11, as observed in Table 10, for a given polymer resin (Example 20 and 21), a higher yarn tenacity with higher elongation was observed for yarn made by optimized conditions. Also, yarn produced from the inventive polymer of Example 15 generated higher tenacity than the yarns produced from the non-inventive polymers of Examples 19, 20, and 21.

orientation processes of the present invention showed slightly higher tensile properties compared to the same samples made by the processes described previously in the prior art literature (i.e., U.S. Pat. No. 6,007,565 (Roby et al.)).

However, the largest and the most important difference between the samples of the present invention and those known in the prior art is in their BSR performance as will be presented in Example 23.

Example 23

In vitro BSR Evaluation of Annealed Braids of the Present Invention vs. those of Prior-Art Teachings (U.S. Pat. No. 6,007,565 (Roby et al.)) under Physiological Conditions This example shows a clear and overwhelming difference in BSR properties between 2-0 braids made based on the present invention versus those described in the prior art teachings (U.S. Pat. No. 6,007,565).

Annealed 2-0 braids as described in Example 22 were placed in a buffer solution modelling physiological conditions of 37° C. and a pH of 7.27. Baseline (Day 0) tensile properties were measured on the suture using an Instron tensile testing unit. Additional samples were removed from the buffer solution every 7 days and Instron tensile tested to determine tensile strength over time. Specifically, two important physical parameters, the straight tensile strength and knot tensile strength, were monitored as a function of hydrolysis time. The Instron crosshead speed was one inch per minute with an initial gauge length of one inch, and a 100 lb. load cell was used. For the Day 0 testing, steel faces were used on the Instron machine, while for all other hydrolysis times rubber faces were used to avoid slippage. After removing samples from the buffer baths, they were allowed to equilibrate to room temperature before testing, and all samples were tested while still wet.

In FIGS. 8A-B, the straight tensile strength in percentages and pounds, respectively, was plotted against the hydrolysis time for the 2-0 braid of the present invention (Example 15), and the series of prior art braids described in Example 22. It was unexpectedly and surprisingly observed that the sample of the present invention showed much longer BSR than any of the samples described by resins and processes in the prior art. This large difference in BSR was not expected based on the initial (time zero) tensile strength values shown in Table

TABLE 12

Tensile Properties of Annealed 2-0 Braids Produced from Prior Art (U.S. Pat. No. 6,007,565 (Roby et al.)) Resins Described in Examples 19-21, and Those of the Present Invention from Example 15

| Polymer ID | Extrusion Conditions | Annealed Braid ID | Braid Diameter (mils) | S/D | Braid Straight Tensile (lbs.) | S/D | % Elong. | S/D | Braid Knot Tensile (lbs.) | S/D |
|---|---|---|---|---|---|---|---|---|---|---|
| Example 15 | Optimized | L051BSHA | 12.83 | 0.97 | 18.6 | 0.65 | 17 | 0.94 | 9.28 | 0.38 |
| Example 19 | Prior art | L071BSHA | 13.10 | 0.53 | 14.7 | 0.22 | 15 | 0.33 | 8.27 | 0.39 |
| Example 20 | Optimized | L069BSHA | 13.42 | 1.03 | 18.4 | 0.46 | 18 | 0.83 | 9.88 | 0.34 |
|  | Prior art | L070BSHA | 12.83 | 1.05 | 15.9 | 0.39 | 15 | 0.65 | 9.16 | 0.42 |
| Example 21 | Optimized | L067BSHA | 12.15 | 0.95 | 18.0 | 0.16 | 17 | 0.40 | 9.10 | 0.28 |
|  | Prior art | L068BSHA | 12.79 | 0.61 | 17.8 | 0.38 | 15 | 0.66 | 8.87 | 0.33 |

Among samples described by prior art teachings, those braids from yarn made by our optimized extrusion and 12, as the initial strength values of the present invention were only slightly higher for the sample of the present invention. This is a significant discovery that would allow the braids of the present invention to be used in surgical applications where longer wound support is needed.

Knot tensile BSR data are shown in FIGS. 9A-B. Similarly, a dramatic difference between the sample of the present invention (Example 15) and the rest of 2-0 braids was observed. While for instance, in FIG. 9A, the samples of the prior art showed the remaining knot strength percentages between 0 and 5% at the 6 week interval, the samples of the present invention showed a significantly higher value of 30%. As in case with straight tensile strength, this is important for surgical applications where longer in vivo wound support is needed.

Additionally, size 2 braids made from the inventive polymer of Example 15 were produced and also placed in a buffer solution modelling physiological conditions of 37° C. and a pH of 7.27 to measure the straight tensile BSR profile, using an Instron testing unit. Straight tensile strength was measured at baseline (0 days), 14 days, 28 days, and 42 days. The BSR curve of this size 2 suture is presented in FIG. 10, showing the strength loss, in pounds, over time. Greater than 25 percent straight tensile strength remained after 42 days indicating utility for slow-to-heal wound approximation.

Example 24

In Vitro/In Vivo BSR Testing and In Vivo Device Absorption
In Vitro/In Vivo BSR Testing In Example 14 and Example 23, BSR results are presented as tested under physiological in vitro conditions utilizing a phosphate buffer solution of pH 7.27 and a temperature of 37° C. These in vitro conditions, or similar variations of, are typically used by those skilled in the art to model in vivo degradation of articles that degrade by hydrolysis, such as those of the present invention. The use of in vitro testing in liue of in vivo testing is recommended to minimize the loss of animal life when evaluating numerous prototypical samples.

To demonstrate how the in vitro methods described in Example 23 model in vivo degradation, two different size 2-0 sutures of the present invention were in vitro and in vivo tested for 42-day % BSR. The two different sets of size 2-0 sutures were made from the polymers of Example 5 and Example 10, and were extruded and braided using the methods described in Example 13.

The in vivo testing was conducted by implanting the sutures subcutaneously in a rat model, and explanting the sutures at 42 days for Instron tensile testing, as described in Example 23. In vitro testing was also conducted using the same conditions and parameters as described in Example 23. Both sets of sutures generated differences in 42-day % BSR between in vitro and in vivo conditions of less than or equal to 2%. The results are summarized in Table 13, which demonstrate the ability of using a physiological in vitro method to model in vivo hydrolytic degradation.

TABLE 13

In vitro and In vivo % BSR Results Summary for 2-0 Sutures of the Present Invention, made from A-B-A Polymers of Two Different B-Segment Compositons

| 2-0 Suture Made From Example Number | B-Segment Molar Composition (% Glycolide/% Lactide) | 42-day % BSR In vitro | 42-day % BSR In vivo |
| --- | --- | --- | --- |
| 10 | 15/85 | 11 | 10 |
| 5 | 60/40 | 30 | 28 |

In Vivo Total Absorption

The sutures of the present invention were also analyzed for in vivo total absorption and tissue reaction analysis. Total absorption is a measure of the amount of material remaining at the implantation site as a function of time. The tissue responses to the sutures of the present invention were comparable to a commercially available random 90/10 glycolide/lactide suture at each study interval. By 119 days post-implantation, both sizes of the suture of the present invention were essentially absorbed with less than 10 percent of the suture material remaining in the extracellular implantation location.

Example 25

Effect of B-Segment Randomness on BSR Properties of the Inventive Sutures

Two segmented A-B-A copolymers of poly(glycolide-co-L(-)-lactide) at an overall molar composition of 90/10 glycolide/lactide ["B" segment molar composition of 50/50 glycolide/lactide] with similar molecular weights but with different randomness of comonomer distribution in the center block as measured by the ACSL using $^1$H-NMR were prepared by the method described in Example 1. The polymer prepared with first stage reaction conditions of 192° C. for 3 hours exhibited an average sequence length of 2.9 whereas the polymer produced with first stage reaction conditions of 174° C. for 2 hours exhibited an average sequence length of 3.1. The resulting IV for both polymers was about 1.4 dL/g. Both polymers were extruded into 56 denier yarn at a die temperature of 246° C., an orientation roll temperature of 84° C. and annealing roll temperature of 115° C. Subsequently the yarn was braided into a USP size 1 braid and hot stretched at a temperature of 101° C. with a draw ratio of 16%. The braid was annealed for 6 hours at a temperature of 124° C. The resulting IV for both braids after annealing was 1.26 dL/g. Braided suture material was placed in phosphate buffer solution (pH 7.27) maintained at 37° C. After 42 days, tensile strength was measured. The braid prepared from the polymer with an average sequence length of 2.9 had an average tensile strength after 42 days in vitro of 11.95 pounds whereas the braid prepared from the polymer with an average sequence length of 3.1 had an average tensile strength of 11.00 pounds.

This example suggests that that the running of the first (prepolymer) stage at higher temperature at a longer time, reduces the average chain sequence length of lactoyl unit in the B-block. This, in turn, may further increase the BSR of the inventive suture compositions.

Although this invention has been shown and described with respect to detailed embodiments thereof, it will be understood by those skilled in the art that various changes in form and detail thereof may be made without departing from the spirit and scope of the claimed invention.

We claim:

1. An absorbable medical device made from an absorbable copolymer of the structure A-B-A comprising end segments A and middle segment B, wherein said end-segments A comprise polymerized glycolide and the middle segment B comprises polymerized glycolide and polymerized lactide, and wherein said middle segment B is fully amorphous and contains about 30 mole percent to about 80 mole percent of polymerized lactide, and about 20 mole percent to about 70 mole percent of polymerized glycolide, and wherein the total amount of polymerized glycolide in the absorbable copolymer is about 88 mole percent to about 92 mole percent of said absorbable copolymer and the total amount of polymerized lactide is about 8 mole percent to about 12 mole percent of said absorbable copolymer and additionally comprising a catalyst with a concentration between about 50,000:1 to about 300,000:1 (moles of monomer:moles of catalyst).

2. The absorbable medical device of claim 1, wherein said device is selected from the group consisting of monofilament sutures, multifilament sutures, barbed sutures, surgical meshes, surgical fabrics, films, surgical tapes, and injection molded articles.

3. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 13 mils, a minimum pre-implantation straight tensile strength of about 17 pounds, and a minimum average straight tensile strength of about 14 pounds at 21 days post-implantation, and, wherein the suture is substantially absorbed in about 120 days or less, post-implantation.

4. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 13 mils, a minimum pre-implantation average straight tensile strength of about 17 pounds, and a minimum average straight tensile strength of about 7 pounds at 35 days post-implantation, and, wherein the suture is substantially absorbed in about 120 days or less, post-implantation.

5. The multifilament absorbable suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 13 mils, a minimum pre-implantation average straight tensile strength of about 17 pounds, and a minimum average straight tensile strength of about 2.3 pounds at 42 days post-implantation, and, wherein the suture is substantially absorbed in about 120 days or less, post-implantation.

6. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 13 mils, a minimum pre-implantation average straight tensile strength of about 17 pounds, and a minimum average straight tensile strength of about 1.0 pounds at 49 days post-implantation, and, wherein the suture is substantially absorbed in about 120 days or less, post-implantation.

7. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 23 mils, a minimum pre-implantation straight tensile strength of about 38 pounds, and a minimum average straight tensile strength of about 30 pounds at 21 days post-implantation, and, wherein the suture is substantially absorbed in about 120 days or less, post-implantation.

8. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 23 mils, a minimum pre-implantation straight tensile strength of about 38 pounds, and a minimum average straight tensile strength of about 20 pounds at 35 days post-implantation, and, wherein the suture is substantially absorbed in about 120 days or less, post-implantation.

9. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the suture has a diameter of about 23 mils, a minimum pre-implantation straight tensile strength of about 38 pounds, and a minimum average straight tensile strength of about 5.5 pounds at 42 days post-implantation, and, wherein the suture is substantially absorbed in about 120 days or less, post-implantation.

10. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the minimum straight tensile strength remaining at 21 days post-implantation is about 80 percent of the initial straight tensile strength value, and wherein the suture is substantially absorbed in about 120 days or less, post-implantation.

11. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the minimum straight tensile strength remaining at 35 days post-implantation is about 50 percent from the initial straight tensile strength value, and, wherein the suture is substantially absorbed in about 120 days or less, post-implantation.

12. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the minimum straight tensile strength remaining at 42 days post-implantation is about 10 percent of the initial straight tensile strength value, and, wherein the suture is substantially absorbed in about 120 days or less, post-implantation.

13. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the minimum straight tensile strength remaining at 49 days post-implantation is about 2 percent of the initial straight tensile strength value, and, wherein the suture is substantially absorbed in about 120 days or less, post-implantation.

14. The absorbable multifilament suture of claim 2, wherein said suture comprises a plurality of filaments, the filaments comprising a poly(lactide-co-glycolide) copolymer, said copolymer comprising about 88 mole percent to about 92 mole percent of polymerized glycolide and about 8 mole percent to about 12 mole percent of polymerized lactide, wherein the oriented yarn has a ratio of percent elongation to tenacity in grams per denier of below 3.5 and having an inherent viscosity, IV, as measured in hexafluoroisopropanol at 25° C. at a concentration of 0.10 g/dL of greater than 1.2 dL/g.

15. The absorbable multifilament suture of claim 2 having a melting point between 212° C. and 216° C., after being subjected to a heat treatment between about 120° C. to 140° C. for at least 6 hours, as measured by Differential Scanning calorimetry (DSC) using the first heat scan with a constant heating rate of 10° C./min.

16. The absorbable multifilament suture of claim 2 having a melting point of at least 210° C., after being subjected to a heat treatment between about 120° C. to 140° C. for at least 6 hours, as measured by Differential Scanning calorimetry (DSC) using the second heat scan with a constant heating rate of 10° C./min.

17. The medical device of claim 1, additionally comprising an antimicrobial agent.

18. The medical device of claim 17, wherein the antimicrobial agent is Triclosan.

19. The medical device of claim 1, additionally comprising a therapeutic agent.

20. The medical device of claim 1, additionally comprising a colorant.

21. The medical device of claim 1, additionally comprising a medically useful sub stance.

22. The absorbable suture of claim 2 additionally comprising a lubricious coating.

23. The medical device of claim 1, wherein said device is manufactured by melt processing.

24. The medical device according to claim 23 wherein said device is manufactured by extrusion or injection molding.

25. The medical device of claim 1, wherein the B-segment contains about 40 to about 70 mole percent polymerized lactide to make the B-segment fully amorphous.

26. The medical device of claim 1, wherein the B-segment contains about 50 to about 60 mole percent of polymerized lactide to make the B-segment fully amorphous.

27. The absorbable copolymer of claim 1, additionally comprising a catalyst with a concentration between about 100,000:1 to about 250,000:1 (moles of monomer:moles of catalyst).

28. The absorbable copolymer of claim 1, additionally comprising a catalyst with a concentration between about 150,000:1 to about 200,000:1 (moles of monomer:moles of catalyst).

29. The absorbable copolymer of claim 1, wherein the catalyst is stannous octoate.

* * * * *